United States Patent
Cosentino et al.

(10) Patent No.: US 11,723,550 B2
(45) Date of Patent: Aug. 15, 2023

(54) IMPEDANCE MEASUREMENT SYSTEM

(71) Applicant: Impedimed Limited, Pinkenba (AU)

(72) Inventors: Jack Gerald Cosentino, Savage, MN (US); Tim Essex, Wakerley (AU); Matthew Joseph Miller, Carlsbad, CA (US)

(*) Notice: Subject to any disclaimer, the term of this patent is extended or adjusted under 35 U.S.C. 154(b) by 0 days.

(21) Appl. No.: 16/845,671

(22) Filed: Apr. 10, 2020

(65) Prior Publication Data

US 2020/0237254 A1 Jul. 30, 2020

Related U.S. Application Data

(63) Continuation of application No. 15/957,563, filed on Apr. 19, 2018, now Pat. No. 10,653,334, which is a (Continued)

(30) Foreign Application Priority Data

Nov. 10, 2015 (AU) .................................. 2015904624

(51) Int. Cl.
*A61B 5/05* (2021.01)
*A61B 5/0537* (2021.01)
(Continued)

(52) U.S. Cl.
CPC .......... *A61B 5/0537* (2013.01); *A61B 5/0004* (2013.01); *A61B 5/0022* (2013.01);
(Continued)

(58) Field of Classification Search
CPC ... A61B 5/0537; A61B 5/4872; A61B 5/4869; A61B 5/053; A61B 5/6887; A61B 5/6829; A61B 5/0531
(Continued)

(56) References Cited

U.S. PATENT DOCUMENTS 4,557,271 A 12/1985 Stoller
5,415,176 A * 5/1995 Sato ..................... A61B 5/0537
177/245
(Continued)

FOREIGN PATENT DOCUMENTS

WO  WO 2013/166426 A1  11/2013

OTHER PUBLICATIONS

International Search Report and Written Opinion dated Dec. 19, 2016 for Application No. PCT/AU2016/051070.

*Primary Examiner* — Joseph A Stoklosa
*Assistant Examiner* — Brian M Antiskay
(74) *Attorney, Agent, or Firm* — Knobbe, Martens, Olson & Bear, LLP

(57) ABSTRACT

A system for performing at least one impedance measurement on a biological subject, the system including a measuring device having a first housing including spaced pairs of foot drive and sense electrodes provided in electrical contact with feet of the subject in use, a second housing including spaced pairs of hand drive and sense electrodes provided in electrical contact with hands of the subject in use, at least one signal generator electrically connected to at least one of the drive electrodes to apply a drive signal to the subject, at least one sensor electrically connected to at least one of the sense electrodes to measure a response signal in the subject and a measuring device processor that at least in part controls the at least one signal generator, receives an indication of a measured response signal from the at least one sensor and generates measurement data indicative of at least one measured impedance value and a client device in communication with the measuring device, the client device being adapted to receive measurement data allowing the client device to display an indicator associated a result of the impedance measurement.

18 Claims, 27 Drawing Sheets

Related U.S. Application Data continuation of application No. PCT/AU2016/051070, filed on Nov. 8, 2016.

(60) Provisional application No. 62/380,267, filed on Aug. 26, 2016, provisional application No. 62/346,941, filed on Jun. 7, 2016.

(51) Int. Cl.
*A61B 5/00* (2006.01)
*A61B 5/0245* (2006.01)
*A61B 5/08* (2006.01)

(52) U.S. Cl.
CPC .......... *A61B 5/0245* (2013.01); *A61B 5/0816* (2013.01); *A61B 5/4872* (2013.01); *A61B 5/4875* (2013.01); *A61B 5/4878* (2013.01); *A61B 5/4881* (2013.01); *A61B 5/6825* (2013.01); *A61B 5/6829* (2013.01); *A61B 5/742* (2013.01); *A61B 5/7405* (2013.01); *A61B 5/7445* (2013.01); *A61B 5/6887* (2013.01); *A61B 2560/0228* (2013.01); *A61B 2560/045* (2013.01); *A61B 2560/0456* (2013.01); *A61B 2562/0209* (2013.01); *A61B 2562/04* (2013.01); *A61B 2562/222* (2013.01); *A61B 2562/227* (2013.01)

(58) Field of Classification Search
USPC ........ 600/372, 382–393, 442, 506–507, 533, 600/547
See application file for complete search history.

(56) References Cited

U.S. PATENT DOCUMENTS

| | | | |
|---|---|---|---|
| 5,817,031 A | 10/1998 | Masuo | |
| 5,860,935 A | 1/1999 | Blaszynski | |
| 6,243,651 B1 | 6/2001 | Masuo | |
| 6,256,532 B1* | 7/2001 | Cha | A61B 5/0537 177/245 |
| 6,354,996 B1 | 3/2002 | Drinan et al. | |
| 6,400,983 B1 | 6/2002 | Cha | |
| 6,490,481 B1 | 12/2002 | Komatsu et al. | |
| 6,507,662 B1 | 1/2003 | Brooks | |
| 6,714,814 B2 | 3/2004 | Yamada | |
| 7,060,914 B2* | 6/2006 | Suzuki | A61B 5/0537 174/54 |
| 7,764,991 B2* | 7/2010 | Yamazaki | A61B 5/4872 600/547 |
| 8,548,556 B2* | 10/2013 | Jensen | A61B 5/4869 600/384 |
| 8,836,345 B2* | 9/2014 | Chetham | A61B 5/053 324/649 |
| 2004/0059242 A1 | 3/2004 | Masuo et al. | |
| 2005/0247494 A1 | 11/2005 | Montagnino | |
| 2007/0038140 A1 | 2/2007 | Masuo et al. | |
| 2007/0208241 A1 | 12/2007 | Drucker | |
| 2008/0183398 A1 | 7/2008 | Petrucelli | |
| 2009/0018464 A1* | 1/2009 | Watanabe | A61B 5/4872 600/547 |
| 2009/0182243 A1 | 7/2009 | Oku | |
| 2009/0204018 A1* | 8/2009 | Tseng | A61B 5/0537 600/547 |
| 2009/0264790 A1* | 10/2009 | Ashida | A61B 5/0537 600/547 |
| 2011/0213268 A1* | 9/2011 | Kosaka | G01G 21/28 600/547 |
| 2011/0295145 A1* | 12/2011 | Sato | A61B 5/0537 600/547 |
| 2012/0172682 A1 | 7/2012 | Linderman | |
| 2013/0023747 A1 | 1/2013 | Karo et al. | |
| 2013/0072813 A1* | 3/2013 | Vogel | A61B 5/6887 600/547 |
| 2014/0058215 A1* | 2/2014 | Hatakeyama | A61B 5/7445 600/301 |
| 2014/0073983 A1* | 3/2014 | Vogel | A61B 5/053 600/547 |
| 2015/0342498 A1 | 12/2015 | Kumagai et al. | |
| 2016/0015276 A1* | 1/2016 | Strauss | A61B 5/0537 600/301 |
| 2016/0051170 A1 | 2/2016 | Lin | |
| 2016/0374618 A1* | 12/2016 | Giovangrandi | A61B 5/7207 600/393 |

\* cited by examiner

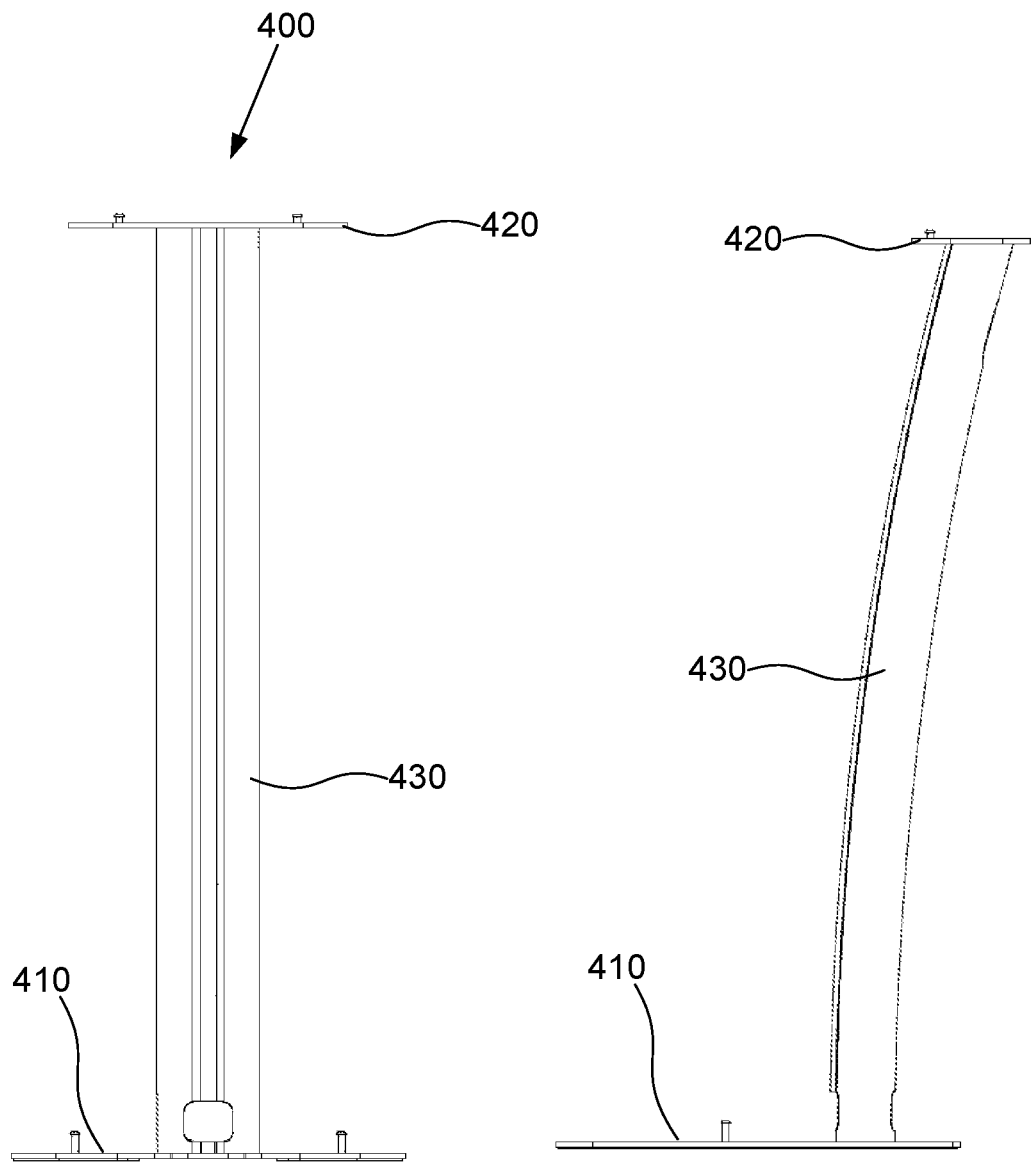

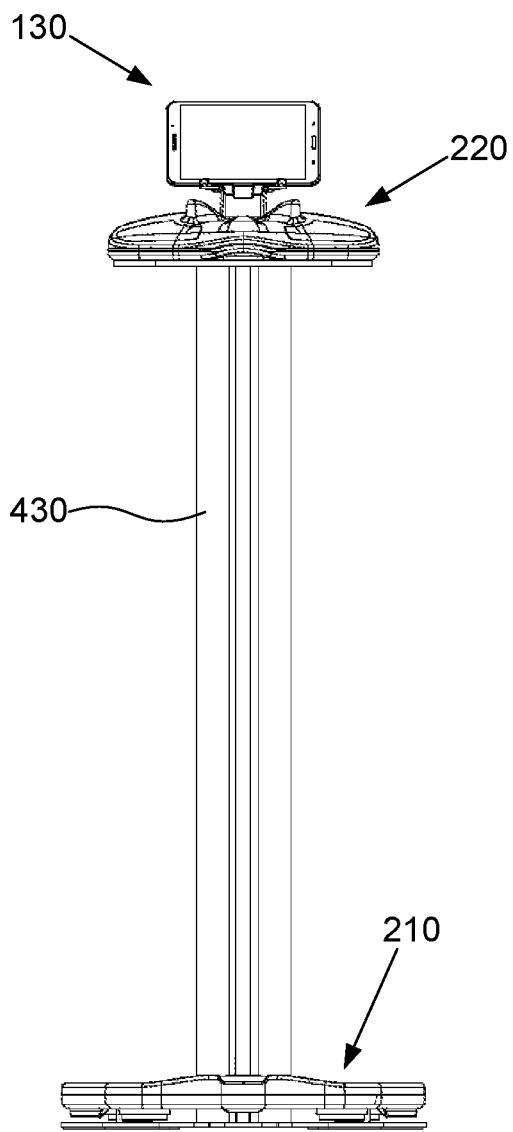 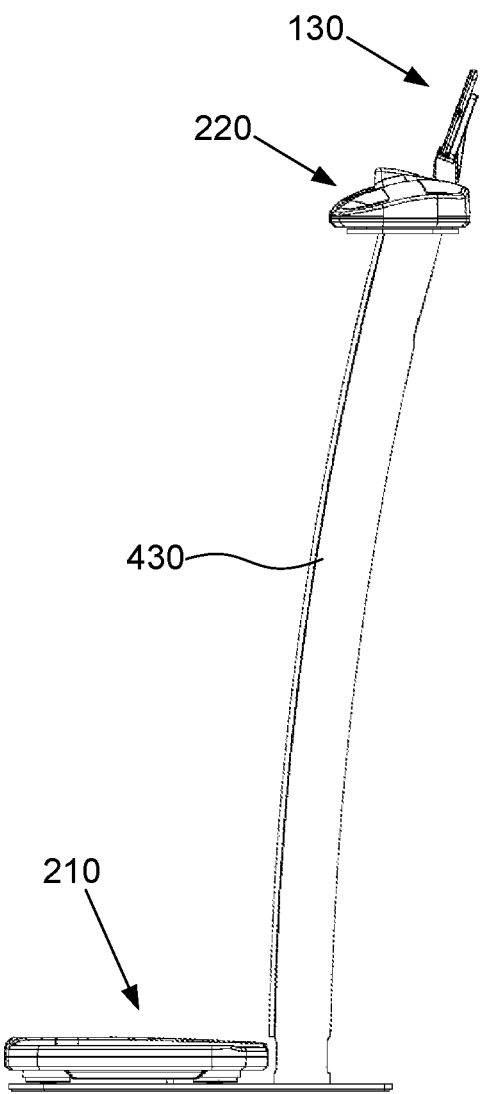
Fig. 4E
Fig. 4F

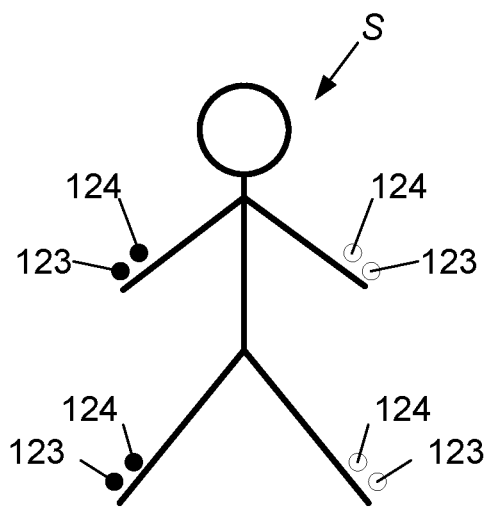
Fig. 5B
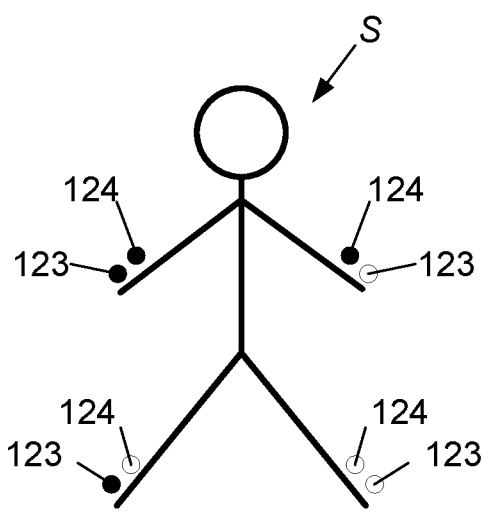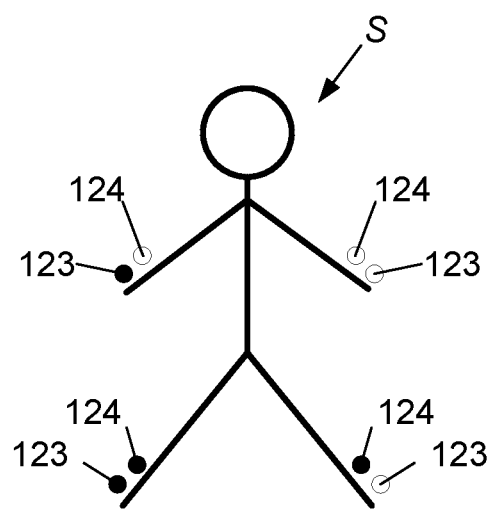
Fig. 5C					Fig. 5D

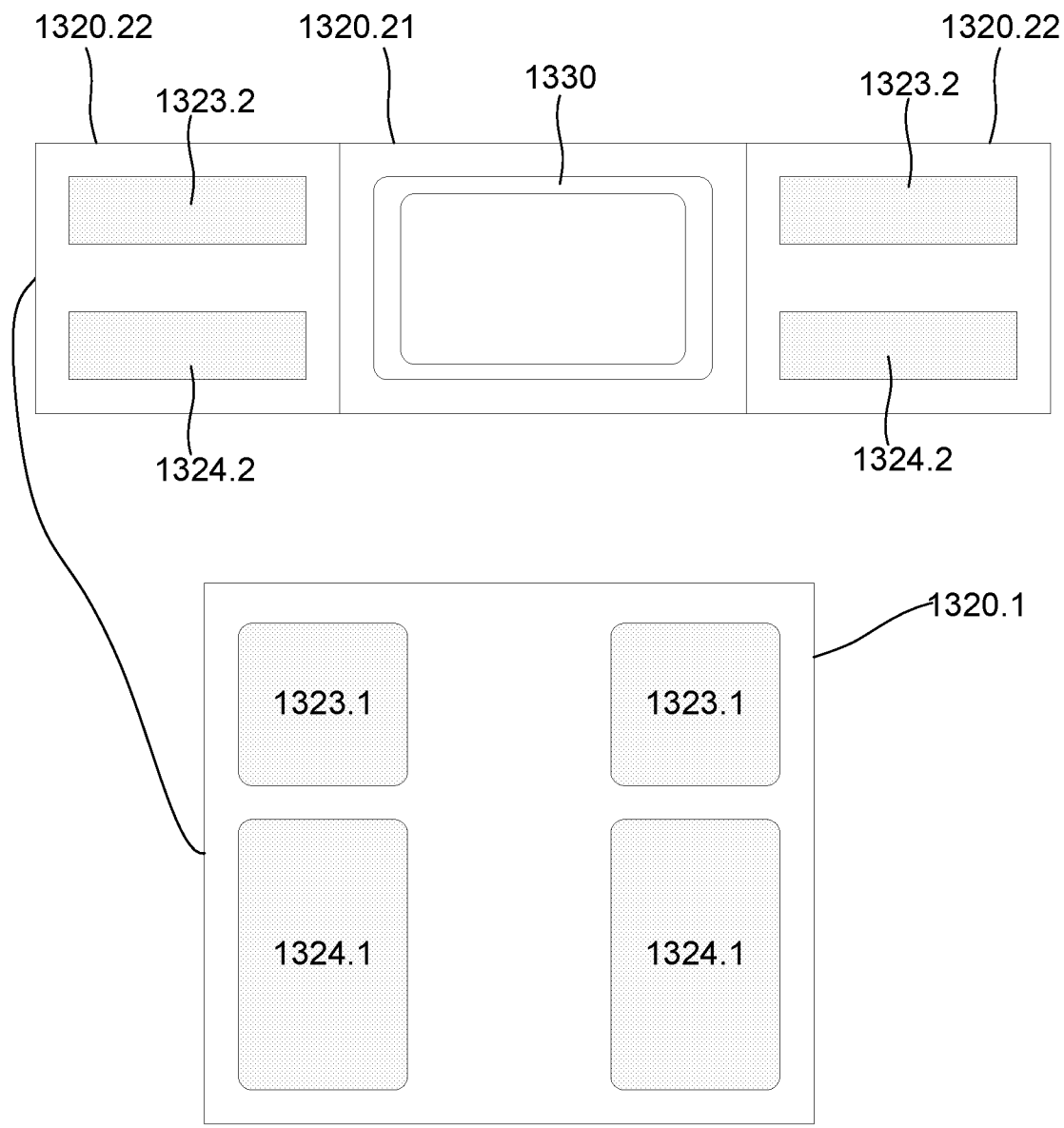
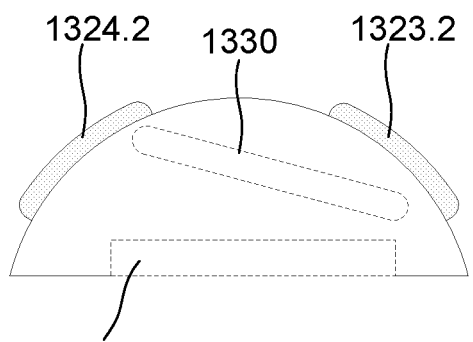
Fig. 13C
Fig. 13D

IMPEDANCE MEASUREMENT SYSTEM

CROSS-REFERENCE TO RELATED APPLICATIONS

This application is a continuation of U.S. patent application Ser. No. 15/957,563, filed Apr. 19, 2018, and published on Aug. 23, 2018 as U.S. Patent Application Publication No. 2018/0235508, which is a continuation of International Patent Application No. PCT/AU2016/051070, filed Nov. 8, 2016, and published in English on May 18, 2017 as WO/2017/079794, which claims the benefit of Australian Patent Application No. 2015904624, filed Nov. 10, 2015, U.S. Provisional Application No. 62/346,941, filed Jun. 7, 2016, and U.S. Provisional Application No. 62/380,267, filed Aug. 26, 2016, each of which are incorporated by reference in their entirety.

BACKGROUND

Embodiments described herein relate to a system and method for performing at least one impedance measurement on a biological subject.

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

WO2007/002991 describes apparatus for performing impedance measurements on a subject. The apparatus includes a first processing system for determining an impedance measurement procedure and determining instructions corresponding to the measurement procedure. A second processing system is provided for receiving the instructions, using the instructions to generate control signals, with the control signals being used to apply one or more signals to the subject. The second processing system then receives first data indicative of the one or more signals applied to the subject, second data indicative of one or more signals measured across the subject and performs at least preliminary processing of the first and second data to thereby allow impedance values to be determined.

SUMMARY

In one broad form embodiments described herein seek to provide a system for performing at least one impedance measurement on a biological subject, the system including:
  a) a measuring device having:
    i) a first housing including spaced pairs of foot drive and sense electrodes provided in electrical contact with feet of the subject in use;
    ii) a second housing including spaced pairs of hand drive and sense electrodes provided in electrical contact with hands of the subject in use;
    iii) at least one signal generator electrically connected to at least one of the drive electrodes to apply a drive signal to the subject;
    iv) at least one sensor electrically connected to at least one of the sense electrodes to measure a response signal in the subject; and,
    v) a measuring device processor that at least in part:
      (1) controls the at least one signal generator;
      (2) receives an indication of a measured response signal from the at least one sensor; and,
      (3) generates measurement data indicative of at least one measured impedance value; and,
  b) a client device in communication with the measuring device, the client device being adapted to receive measurement data allowing the client device to display an indicator associated a result of the impedance measurement.

Typically the drive and sense electrodes are spaced apart metal plates.

Typically the foot drive and sense electrodes are spaced apart by at least one of:
  a) at least 8 cm;
  b) at least 8.2 cm;
  c) at least 8.4 cm;
  d) up to 9 cm;
  e) up to 8.8 cm;
  f) up to 8.6 cm;
  g) between 8 cm and 9 cm;
  h) between 8.2 cm and 8.8 cm;
  i) between 8.4 cm and 8.6 cm; and,
  j) approximately 8.5 cm.

Typically the foot drive electrode has a surface area that is at least one of:
  a) at least 110 cm;
  b) at least 115 cm;
  c) at least 120 cm;
  d) at least 122 cm;
  e) up to 140 cm;
  f) up to 135 cm;
  g) up to 130 cm;
  h) up to 218 cm;
  i) between 110 $cm^2$ and 140 $cm^2$;
  j) between 115 $cm^2$ and 135 $cm^2$;
  k) between 120 $cm^2$ and 130 $cm^2$;
  l) between 122 $cm^2$ and 128 $cm^2$;
  m) approximately 125 $cm^2$; and,
  n) approximately 124.3 $cm^2$.

Typically the foot sense electrode has a surface area that is at least one of:
  a) at least 35 cm;
  b) at least 40 cm;
  c) at least 45 cm;
  d) at least 50 cm;
  e) up to 70 cm;
  f) up to 65 cm;
  g) up to 60 cm;
  h) up to 55 cm;
  i) between 35 $cm^2$ and 70 $cm^2$;
  j) between 40 $cm^2$ and 65 $cm^2$;
  k) between 45 $cm^2$ and 60 $cm^2$;
  l) between 50 $cm^2$ and 55 $cm^2$;
  m) approximately 53 $cm^2$; and,
  n) approximately 52.6 $cm^2$.

Typically the first housing includes a raised lip extending at least partially around each pair of foot drive and sense electrodes to thereby guide positioning of a subject's foot relative to the foot drive and sense electrodes in use.

Typically the raised lip is configured to engage at least a heel of the subject.

Typically the first housing includes feet that support the first housing spaced from a surface.

Typically the feet engage load cells mounted within the first housing, the measuring device processor being adapted to determine a weight of a subject standing on the first housing.

Typically the first housing includes:
  a) a rigid internal plate; and, b) four foot assemblies, each foot assembly including:
  i) a load cell mounting on an underside of the plate;
  ii) a foot member; and,
  iii) a load cell coupled to the load cell mounting and the foot member so that the load cell deforms upon application of a load to the rigid plate.

Typically the load cell mounting includes a cylindrical body extending from the plate, the foot member at least partially positioned in and axially movable within the cylindrical body.

Typically the first housing includes supporting ridges extending along underside lateral edges of the first housing.

Typically the hand drive and sense electrodes in each pair are spaced apart by at least one of:
a) at least 3 cm;
b) at least 3.2 cm;
c) at least 3.4 cm;
d) up to 4 cm;
e) up to 3.8 cm;
f) up to 3.6 cm;
g) between 3 cm and 4 cm;
h) between 3.2 cm and 3.8 cm;
i) between 3.4 cm and 3.6 cm; and,
j) approximately 3.5 cm.

Typically the hand drive electrode has a surface area that is at least one of:
a) at least 35 cm;
b) at least 38 cm;
c) at least 40 cm;
d) at least 41 cm;
e) up to 50 cm;
f) up to 45 cm;
g) up to 43 cm;
h) up to 42 cm;
i) between 35 $cm^2$ and 50 $cm^2$;
j) between 38 $cm^2$ and 45 $cm^2$;
k) between 40 $cm^2$ and 43 $cm^2$;
l) between 41 $cm^2$ and 42 $cm^2$;
m) approximately 41 $cm^2$; and,
n) approximately 41.4 $cm^2$.

Typically the hand sense electrode has a surface area that is at least one of:
a) at least 35 cm;
b) at least 40 cm;
c) at least 45 cm;
d) at least 46 cm;
e) up to 55 cm;
f) up to 50 cm;
g) up to 49 cm;
h) up to 48 cm;
i) between 35 $cm^2$ and 55 $cm^2$;
j) between 40 $cm^2$ and 50 $cm^2$;
k) between 45 $cm^2$ and 49 $cm^2$;
l) between 46 $cm^2$ and 48 $cm^2$;
m) approximately 47 $cm^2$; and,
n) approximately 46.8 $cm^2$.

Typically the second housing is shaped to at least partially conform to a shape of a subject's hands.

Typically the second housing has a curved upper surface.

Typically a radius of curvature of the hand drive electrode is different to a radius of curvature of the hand sense electrode.

Typically a radius of curvature of the hand drive electrode is at least one of:
a) at least 100 mm;
b) at least 110 mm;
c) at least 115 mm;
d) at least 118 mm;
e) up to 150 mm;
f) up to 130 mm;
g) up to 125 mm;
h) up to 122 mm;
i) between 100 mm and 150 mm;
j) between 110 mm and 130 mm;
k) between 115 mm and 125 mm;
l) between 118 mm and 122 mm;
m) approximately 120 mm; and,
n) approximately 119.5 mm;

Typically a radius of curvature of the hand sense electrode is at least one of:
a) at least 180 mm;
b) at least 200 mm;
c) at least 210 mm;
d) at least 215 mm;
e) up to 260 mm;
f) up to 240 mm;
g) up to 230 mm;
h) up to 225 mm;
i) between 180 mm and 260 mm;
j) between 200 mm and 240 mm;
k) between 210 mm and 230 mm;
l) between 215 mm and 225 mm;
m) approximately 220 mm; and,
n) approximately 218 mm.

Typically the second housing includes a raised portion between each pair of hand drive and sense electrodes, the raised portion defining thumb recesses to thereby guide positioning of a subject's hands relative to each pair of hand drive and sense electrodes in use.

Typically raised portion includes two ridges, each ridge extending towards a respective hand sense electrodes, and being adapted to be positioned between a subject's thumb and forefinger.

Typically system includes a support that supports a client device, the support being removably mounted to the second housing.

Typically the support includes:
a) a mounting that removably couples to the second housing; and,
b) a frame that receives the client device.

Typically the frame is pivotally coupled to the mounting to allow the frame to be at least one of:
a) tilted relative to the mounting; and,
b) rotated relative to the mounting.

Typically the client device is at least one of a tablet and a smartphone.

Typically the system includes a stand including:
a) a base that supports the first housing;
b) a platform that supports the second housing; and,
c) a leg coupled to the base and platform to support the platform relative to the base.

Typically the leg is curved so that a centre of the platform is offset from a centre of the base.

Typically the leg includes a cavity that receives a lead extending between the first and second housings.

Typically the platform is spaced from the base by a vertical distance of at least one of:
a) at least 100 cm;
b) at least 103 cm;
c) at least 104 cm;
d) at least 105 cm;
e) up to 110 cm;
f) up to 108 cm;
g) up to 107 cm;

h) up to 106 cm;
i) between 100 cm and 110 cm;
j) between 103 cm and 108 cm;
k) between 104 cm and 107 cm;
l) between 105 cm and 106 cm;
m) approximately 105.5 cm; and,
n) 105.4 cm.

Typically at least one of the first and second housings include keyhole mountings, allowing the at least one of the first and second housings to be removably mounted to the base and platform respectively.

Typically the system includes:
a) four signal generators, each signal generator being electrically connected to a respective drive electrode; and,
b) four sensors, each sensor being electrically connected to at least one of the sense electrodes to measure a response signal in the subject.

Typically the measuring device processor selectively controls the four signal generators and four sensors to perform a sequence of impedance measurements, the impedance measurements including:
a) segmental impedance measurements; and,
b) whole of body impedance measurements.

Typically the system includes four sensors attached to the drive electrodes to allow the drive electrodes to be used in sensing body signals.

Typically the first and second housings contain respective circuit boards interconnected via a lead.

Typically the measuring device includes a communications module for communicating with the client device.

Typically the measuring device processor communicates with the client device to at least one of:
a) determine the at least one measurement to be performed;
b) provide a measurement indication to the client device, the measurement indication being indicative of a measurement being performed;
c) provide measurement data to the client device, the measurement data being indicative of at least one of:
  i) measured signals;
  ii) a body parameter value derived from the measured signals, the body parameter including at least one of:
    (1) a respiration parameter;
    (2) a cardiac parameter;
    (3) an impedance parameter; and,
    (4) a weight parameter.

Typically the measuring device processor:
a) determines a presence of a subject in accordance with signals from at least one of the load cells and the at least one sensor;
b) commences at least one measurement procedure;
c) provides a measurement indication to the client device, the client device being responsive to the measurement indication to display an indication of at least one of:
  i) information regarding the measurement process;
  ii) measured signals;
  iii) a body parameter value;
  iv) a body status indicator;
  v) instructions to the subject; and,
  vi) a question for the subject.
d) performs the measurement; and,
e) provides measurement data to the client device, the measurement data being indicative of at least one of:
  i) measured signals; and,
  ii) a body parameter value derived from the measured signals, the body parameter including at least one of:
    (1) a respiration parameter;
    (2) a cardiac parameter;
    (3) an impedance parameter; and,
    (4) a weight parameter.

Typically the measuring device processor:
a) detects when a subject is standing on the foot unit in accordance with signals from at least one of the load cells; and,
b) causes a weight measurement procedure to be performed using signals from the load cells.

Typically the measuring device processor:
a) detects when a subject's hands and feet are positioned in contact with the hand and feet electrodes in accordance with signals from the at least one sensor; and,
b) causes a measurement procedure to be performed including at least one of:
  i) an impedance measurement procedure;
  ii) a cardiac measurement procedure; and,
  iii) a respiration measurement procedure.

Typically the measuring device performs a cardiac or respiration measurement procedure by:
a) using at least one sensor to measure at least one body signal in the subject via at least the sense electrodes; and,
b) analysing the body signals to determine at least one of:
  i) a respiration parameter value; and,
  ii) a cardiac parameter.

Typically the measuring device processor:
a) detects when a subject is standing on the foot unit in accordance with signals from at least one of the load cells;
b) provides weight measurement indication to the client device, the client device being responsive to the weight measurement indication to instruct the subject to stand for a weight measurement;
c) performs the weight measurement;
d) provides a body measurement indication to the client device, the client device being responsive to the body measurement indication to instruct the subject to place their feet and hands on the respective electrodes;
e) detects when a subject's hands and feet are positioned in contact with the hand and feet electrodes in accordance with signals from the at least one sensor;
f) commences a measurement procedure to be performed including at least one of:
  i) an impedance measurement procedure;
  ii) a cardiac measurement procedure; and,
  iii) a respiration measurement procedure; and,
g) provides measurement data to the client device, the client device being responsive to the measurement data to:
  i) generate at least one body status indicator using the measurement data; and,
  ii) display an indication of the at least one body status indicator to the subject.

In one broad form embodiments described herein seek to provide a method for performing at least one impedance measurement on a biological subject, the system including:
a) using a measuring device having:
  i) a first housing including spaced pairs of foot drive and sense electrodes provided in electrical contact with feet of the subject in use;
  ii) a second housing including spaced pairs of hand drive and sense electrodes provided in electrical contact with hands of the subject in use;

iii) at least one signal generator electrically connected to at least one of the drive electrodes to apply a drive signal to the subject;
iv) at least one sensor electrically connected to at least one of the sense electrodes to measure a response signal in the subject; and,
v) a measuring device processor that at least in part:
   (1) controls the at least one signal generator;
   (2) receives an indication of a measured response signal from the at least one sensor; and,
   (3) generates measurement data indicative of at least one measured impedance value; and,
vi) using a client device in communication with the measuring device, the client device being adapted to receive measurement data allowing the client device to display an indicator associated a result of the impedance measurement.

In one broad form embodiments described herein seek to provide a system for performing at least one impedance measurement on a biological subject, wherein the system including a measuring device processor that:
a) determines a presence of a subject in accordance with signals from at least one of a load cell and at least one sensor;
b) provides a measurement indication to a client device, the client device being responsive to the measurement indication to display an indication of at least one of:
   i) information regarding the measurement process;
   ii) measured signals;
   iii) a body parameter value;
   iv) a body status indicator;
   v) instructions to the subject; and,
   vi) a question for the subject.
c) causes the measurement to be performed; and,
d) provides measurement data to the client device, the measurement data being indicative of at least one of:
   i) measured signals; and,
   ii) a body parameter value derived from the measured signals, the body parameter including at least one of:
      (1) a respiration parameter;
      (2) a cardiac parameter;
      (3) an impedance parameter; and,
      (4) a weight parameter.

In one broad form embodiments described herein seek to provide a method for performing at least one impedance measurement on a biological subject, wherein the method includes, in a measuring device processor:
a) determining a presence of a subject in accordance with signals from at least one of a load cell and at least one sensor;
b) providing a measurement indication to a client device, the client device being responsive to the measurement indication to display an indication of at least one of:
   i) information regarding the measurement process;
   ii) measured signals;
   iii) a body parameter value;
   iv) a body status indicator;
   v) instructions to the subject; and,
   vi) a question for the subject.
c) causing the measurement to be performed; and,
d) providing measurement data to the client device, the measurement data being indicative of at least one of:
   i) measured signals;
   ii) a body parameter value derived from the measured signals, the body parameter including at least one of:
      (1) a respiration parameter;
      (2) a cardiac parameter;
      (3) an impedance parameter; and,
      (4) a weight parameter.

It will be appreciated that the broad forms of the embodiments described herein can be used in conjunction and/or independently, and reference to separate broad forms in not intended to be limiting.

BRIEF DESCRIPTION OF THE DRAWINGS

An example of the embodiments described herein will now be described with reference to the accompanying drawings, in which:—

FIG. 4B is a schematic front view of the stand of FIG. 4A;

FIG. 4C is a schematic side view of the stand of FIG. 4A;

FIG. 4E is a schematic front view of the system of FIG. 4D;

FIG. 4F is a schematic side view of the system of FIG. 4D;

FIGS. 5B to 5D are schematic diagrams showing example electrode configurations in use for the measuring system of FIG. 5A;

FIG. 13C is a schematic diagram of an example of an alternative impedance measuring system; and, FIG. 13D is a schematic diagram end view of the second housing of the connectivity module of FIG. 13C.

DETAILED DESCRIPTION OF THE PREFERRED EMBODIMENTS

Figure 1:
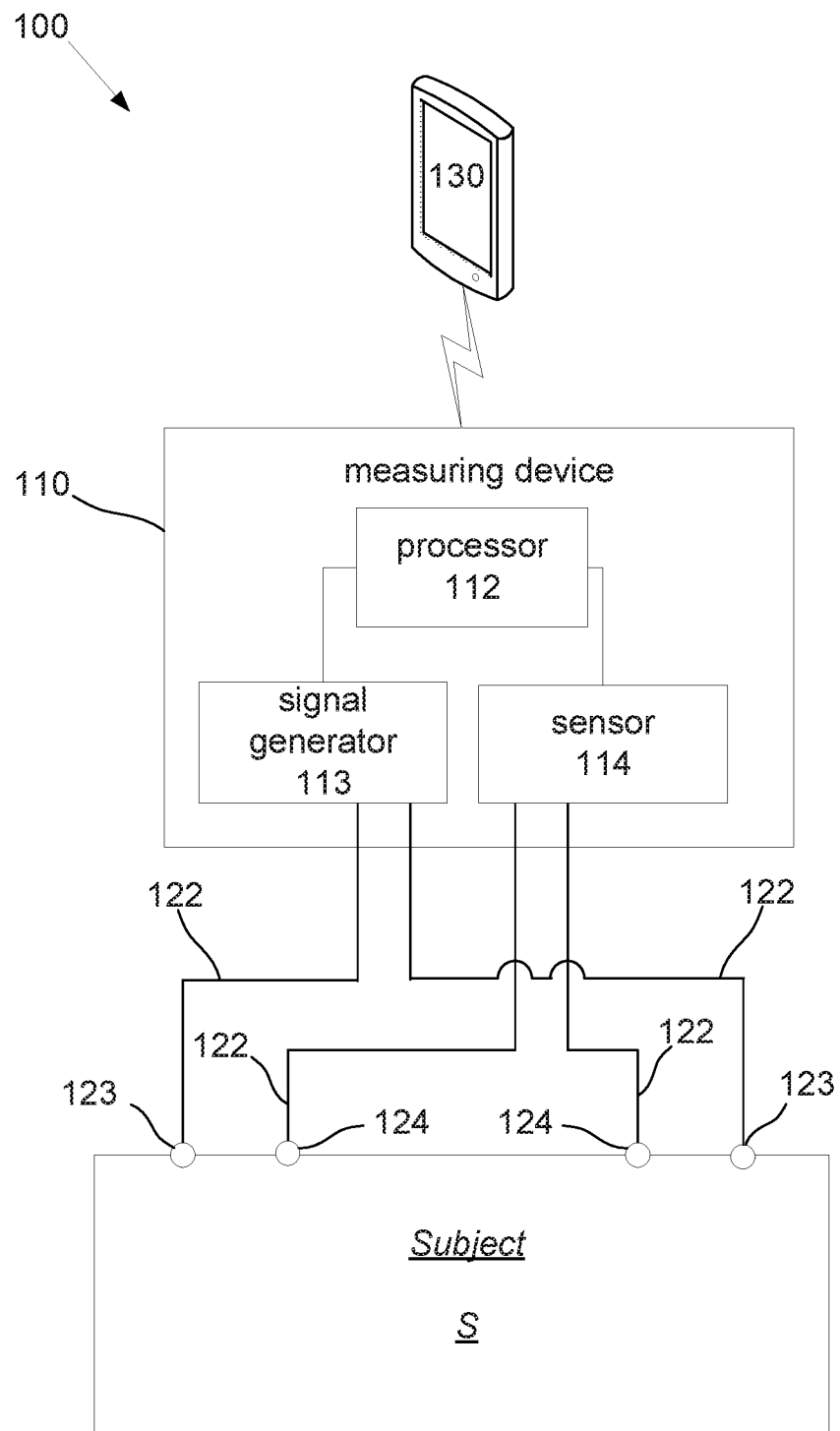
FIG. 1 is a schematic diagram of an example of a system for performing at least one impedance measurement on a subject.

An example of apparatus suitable for performing at least one impedance measurement on a biological subject will now be described with reference to FIG. 1.

In this example, the measuring system 100 includes an impedance measuring device 110, including a measuring device processor 112 coupled to at least one signal generator 113 and at least one sensor 114, which are in turn coupled to respective drive and sense electrodes 123, 124, via connections, such as wires or leads 122. Two drive and two sense electrodes are shown in this example, but this is not intended to be limiting and additional electrodes can be provided as will be described in more detail below.

In use, the signal generator 113 generates a drive signal, which is applied to the subject S via the drive electrodes 123, whilst the sensor 114 measures a response signal via the sense electrodes 124. Thus, in use, the measuring device processor 112 controls the at least one signal generator 113 to cause drive signals to be applied to a subject, with a response signal being measured using the at least one sensor 114, allowing the measuring device processor 112 to generate measurement data indicative of at least one measured impedance value. The measurement data can include an indication of the measured signals and/or impedance values derived therefrom, as will be described in more detail below.

The measuring device 110 is typically in communication with a client device 130, such as a portable computer system, mobile phone, tablet or the like, allowing the measurement data to be provided to the client device 130, in turn allowing the client device to display an indicator associated a result of the impedance measurement.

As part of this, the client device 130 can receive measurement data including an indication of the drive/sense signals and/or measured impedance values. The client device 130 can then optionally perform further processing, for example to determine the impedance indicators, such as indicators of body composition or the like. The client device 130 can also combine impedance values or indicators with other information, including indications of disease states or physical characteristics of the subject, determined either by manual user input or based on signals from one or more physical characteristic sensors. This allows the client device 130 to generate collected subject data, which can then be transferred to a remote processing system, such as a server or the like for further analysis and/or storage. Additionally, the client device 130 can analyse historical measurement data, either stored locally or retrieved from the server, allowing changes in measured values over time to be monitored, as will be described in more detail below.

Figure 2:
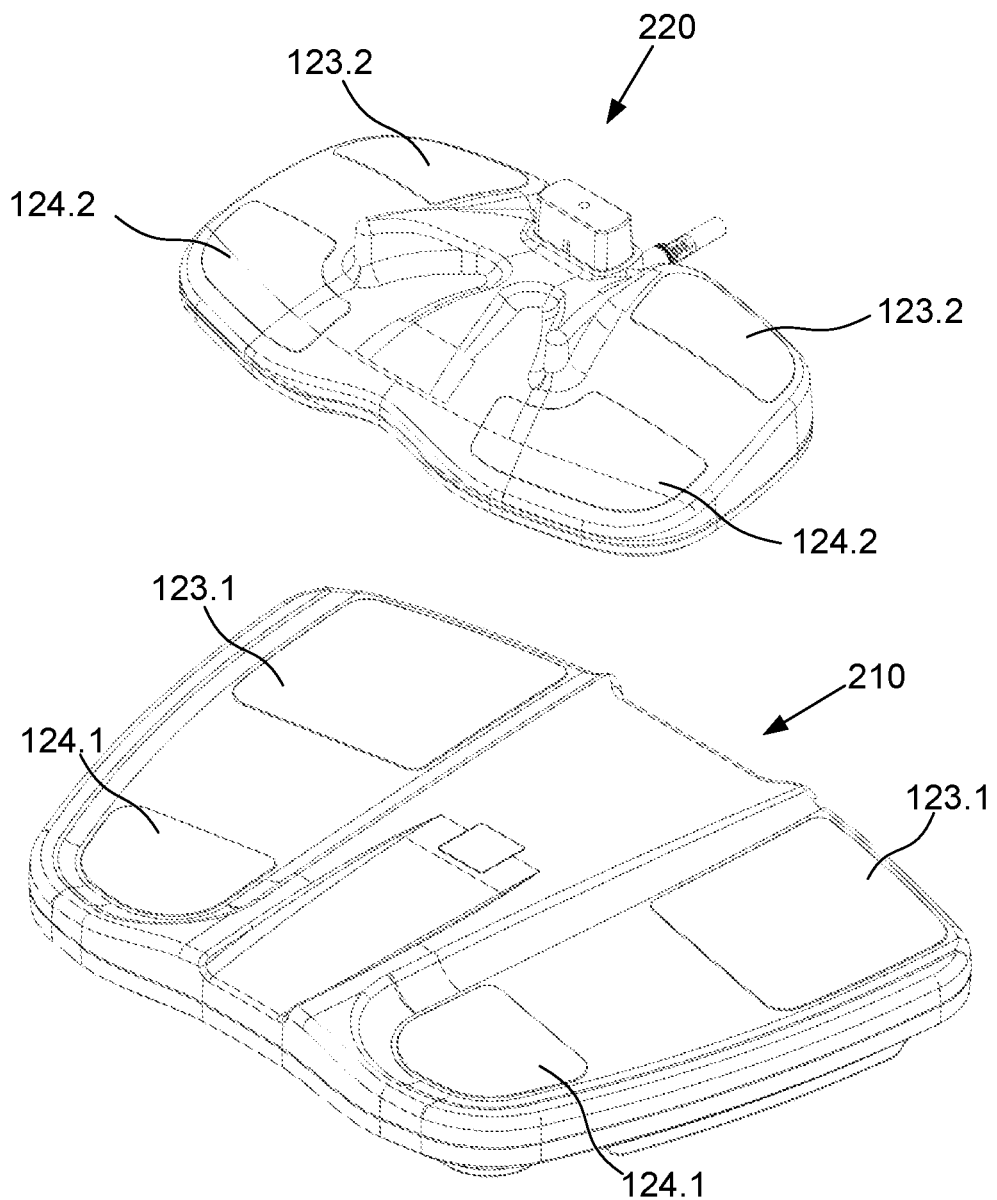
FIG. 2 is a schematic perspective view of an example of a measuring device housing.
Figure 3A:
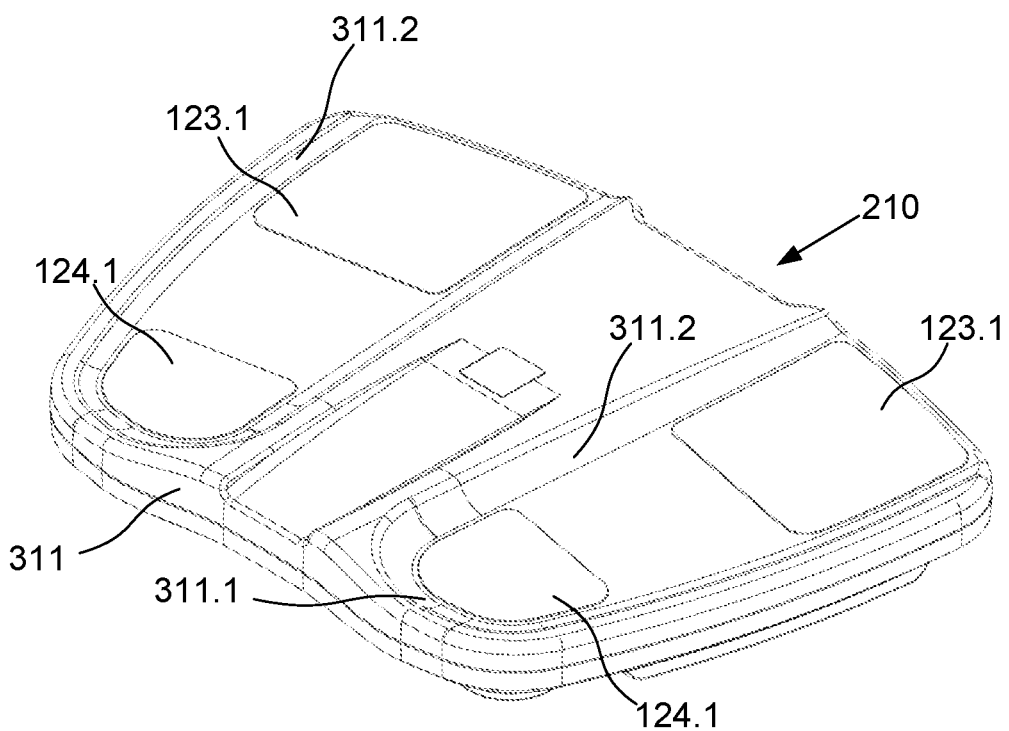
FIG. 3A is a schematic perspective view of a specific example of a first housing.
Figure 3B:
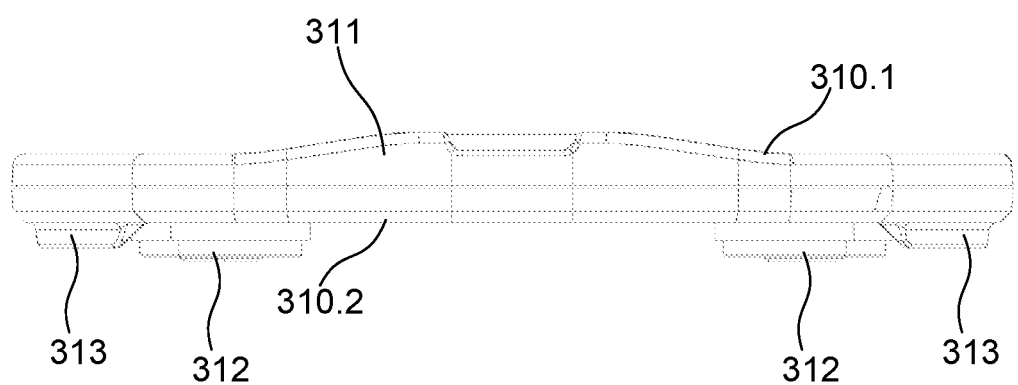
FIG. 3B is a schematic front view of the first housing of FIG. 3A.
Figure 3C:
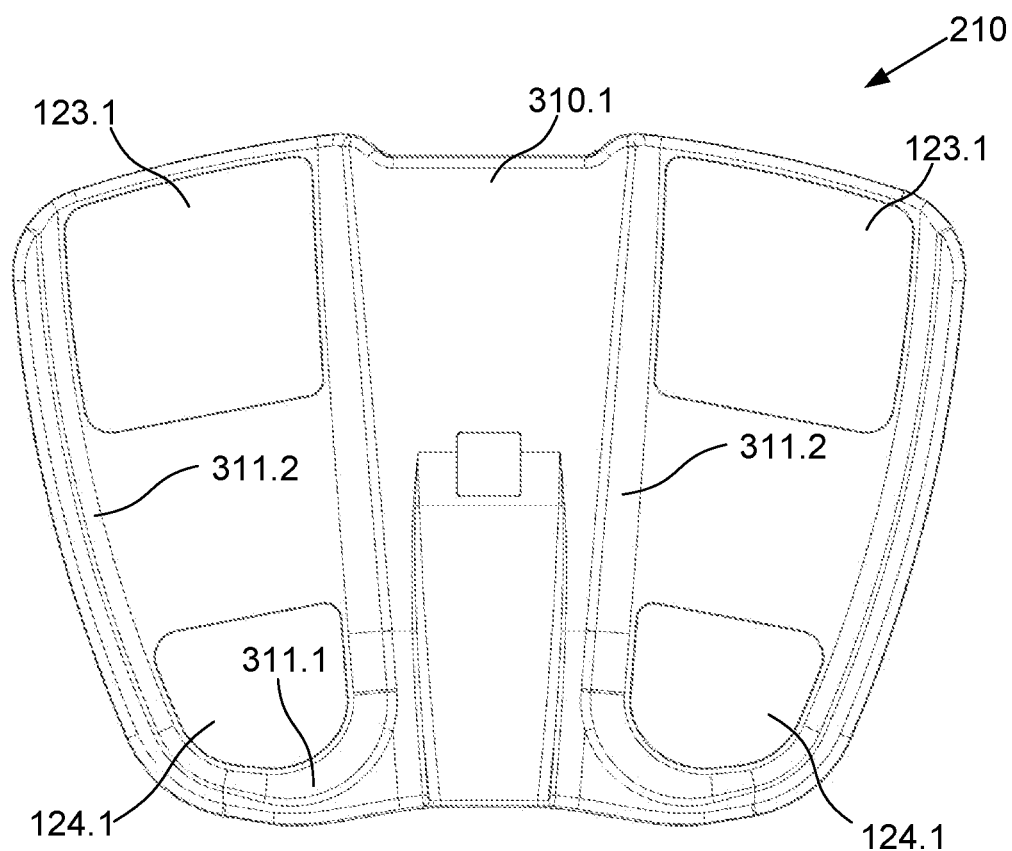
FIG. 3C is a schematic plan view of the first housing of FIG. 3A.
Figure 3D:
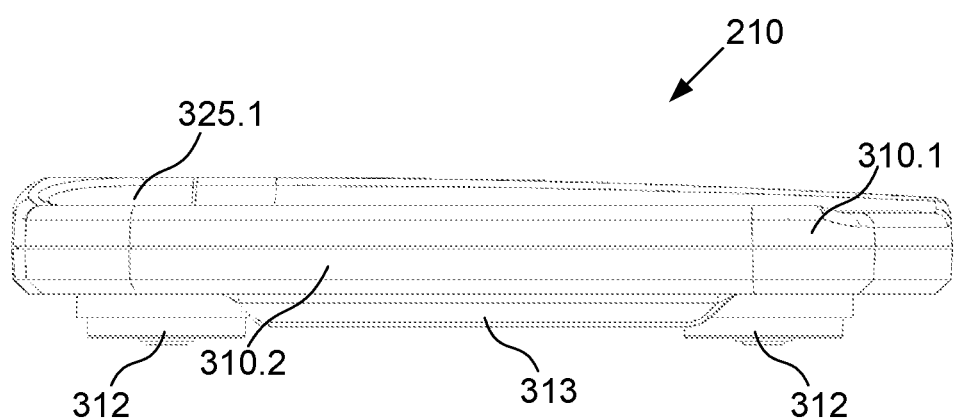
FIG. 3D is a schematic side view of the first housing of FIG. 3A.
Figure 3E:
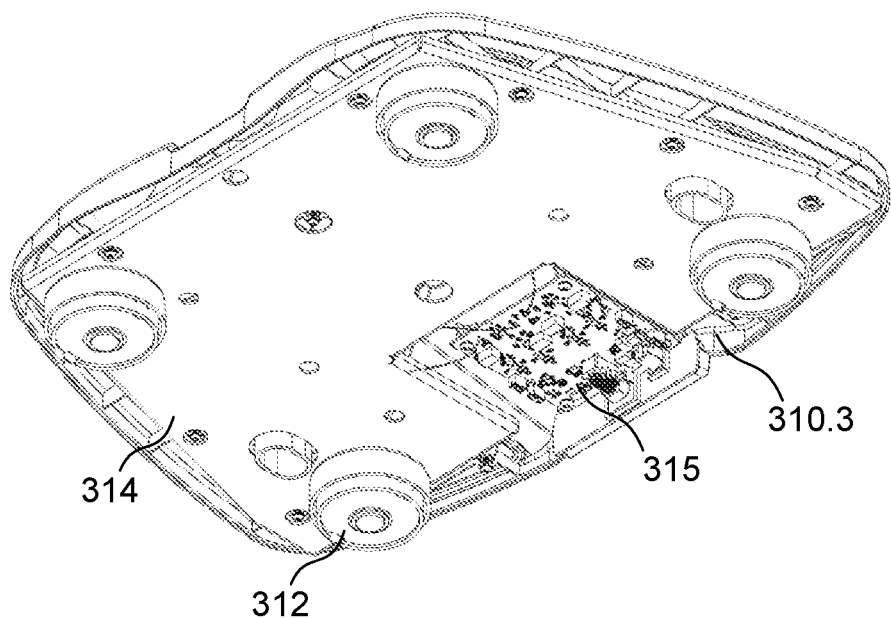
FIG. 3E is a schematic underside perspective view of the first housing of FIG. 3A with a base removed.
Figure 3F:
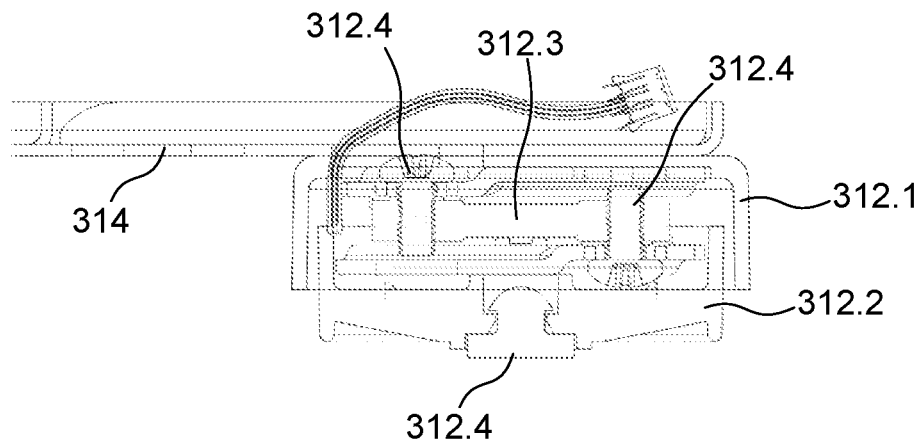
FIG. 3F is a schematic cut away side view of a load cell mounted the first housing of FIG. 3A.
Figure 3G:
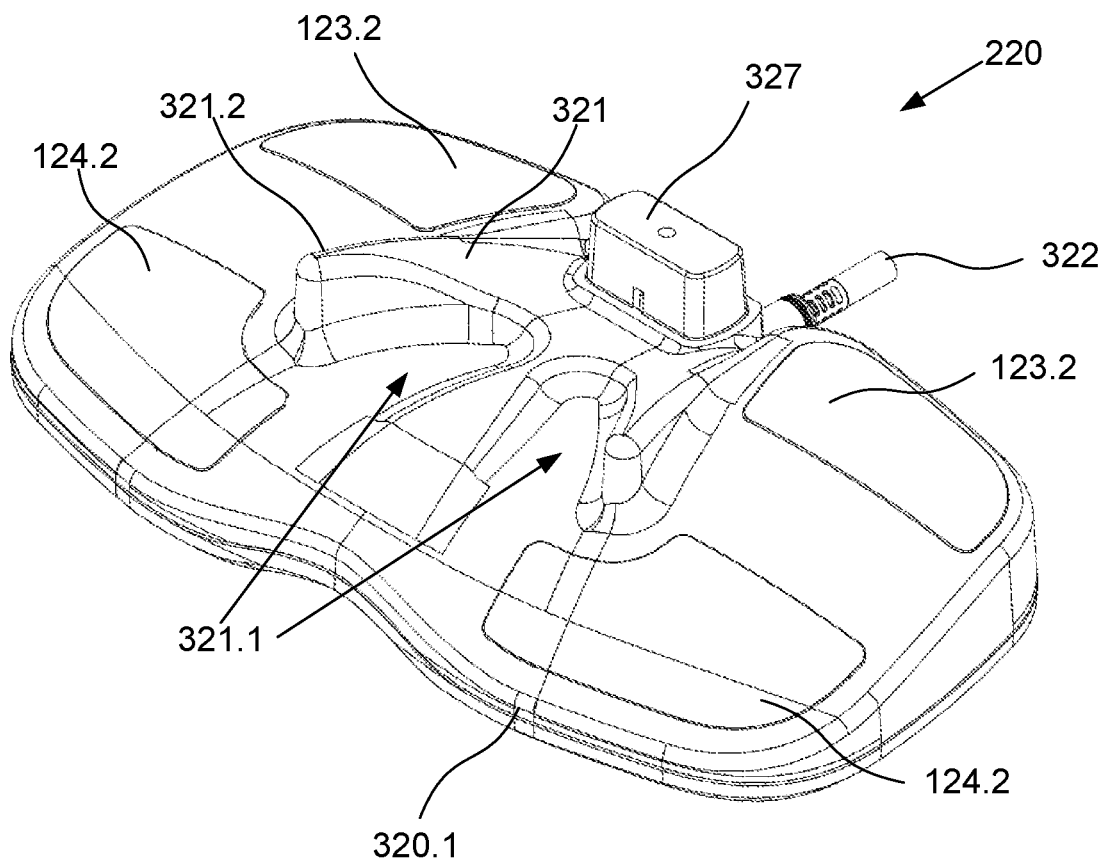
FIG. 3G is a schematic perspective view of a specific example of a second housing.
Figure 3H:
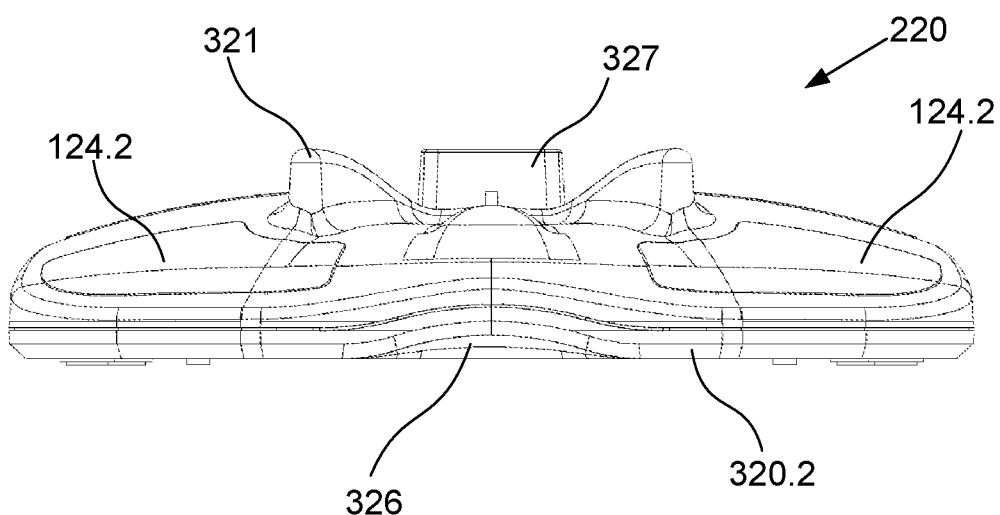
FIG. 3H is a schematic front view of the second housing of FIG. 3G.
Figure 3I:
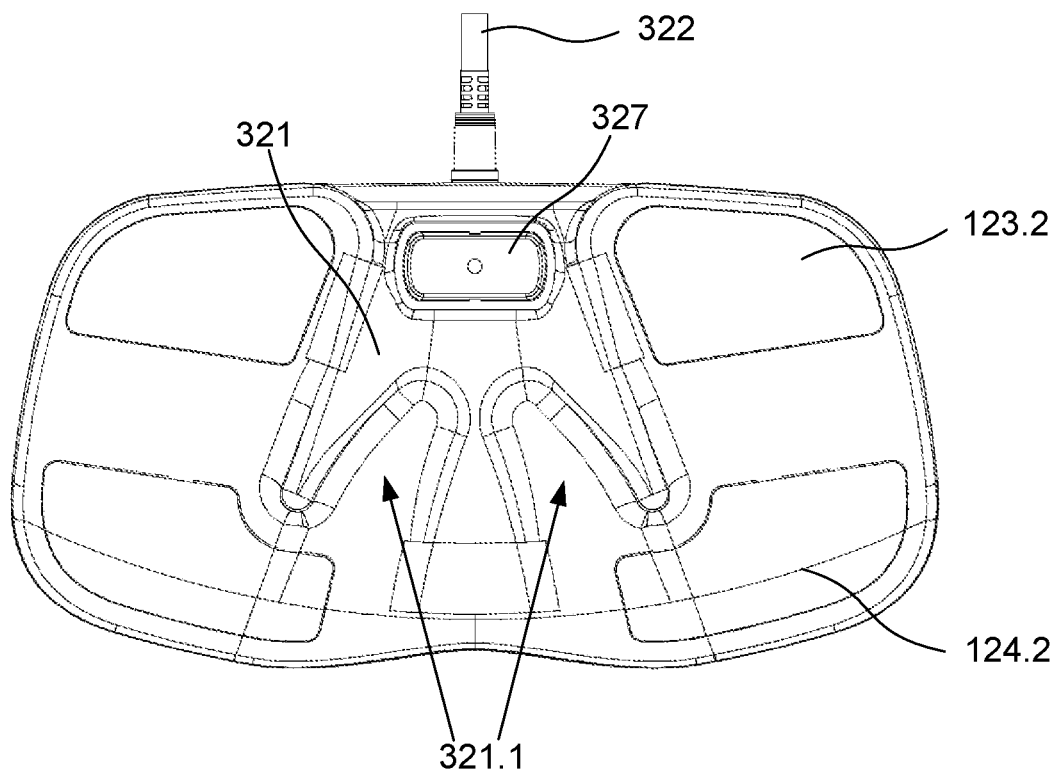
FIG. 3I is a schematic plan view of the second housing of FIG. 3G.
Figure 3J:
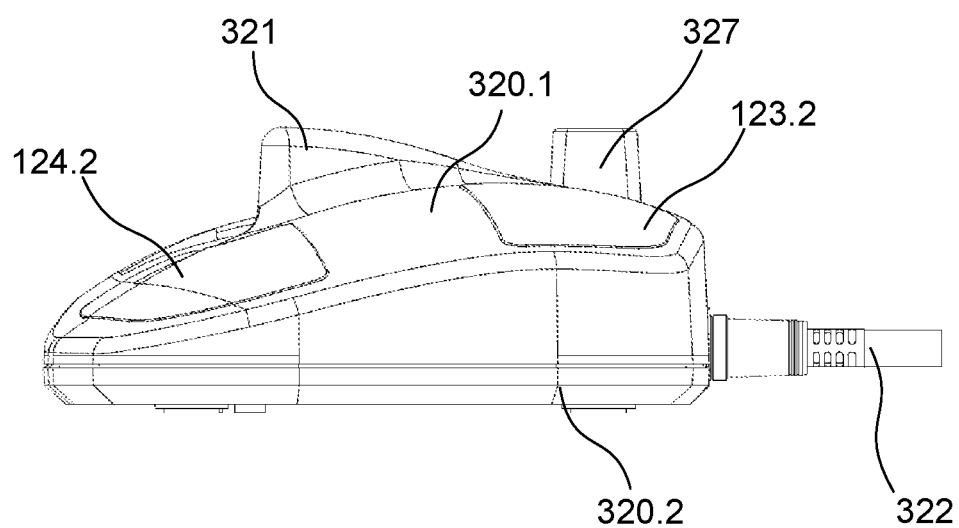
FIG. 3J is a schematic side view of the second housing of FIG. 3G.
Figure 3K:
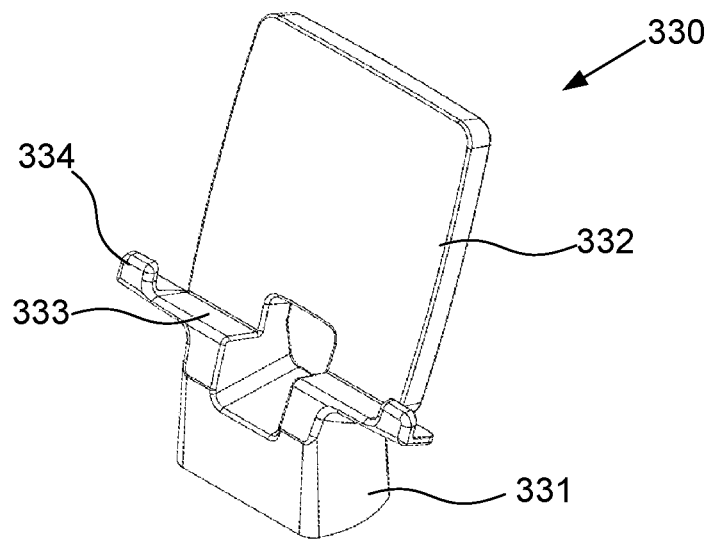
FIG. 3K is a schematic perspective view of a client device support.
Figure 3L:
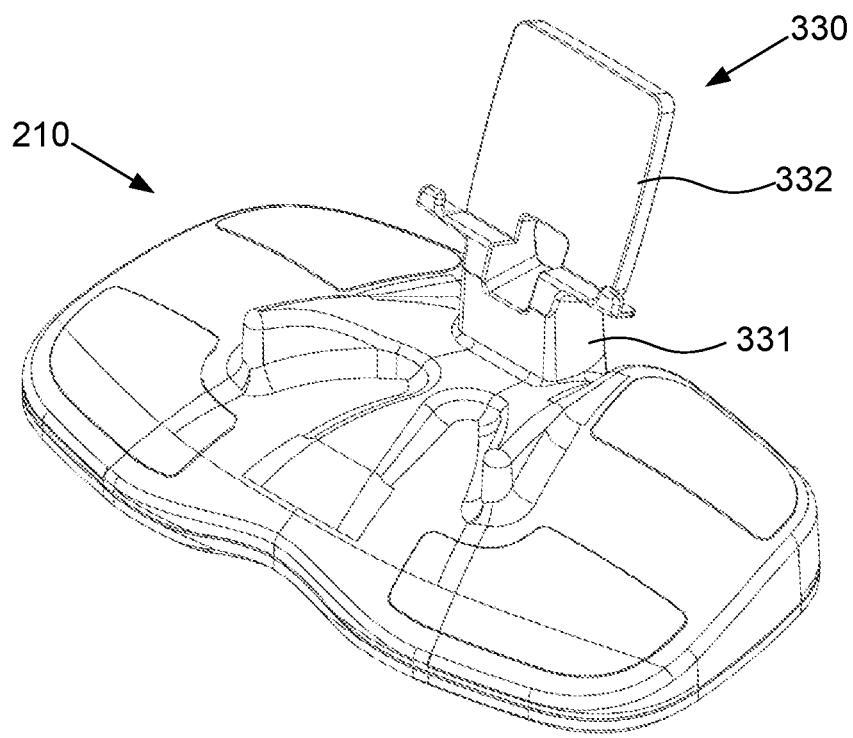
FIG. 3L is a schematic perspective view of the client device support of FIG. 3K mounted to the second housing of FIG. 3G.
Figure 3M:
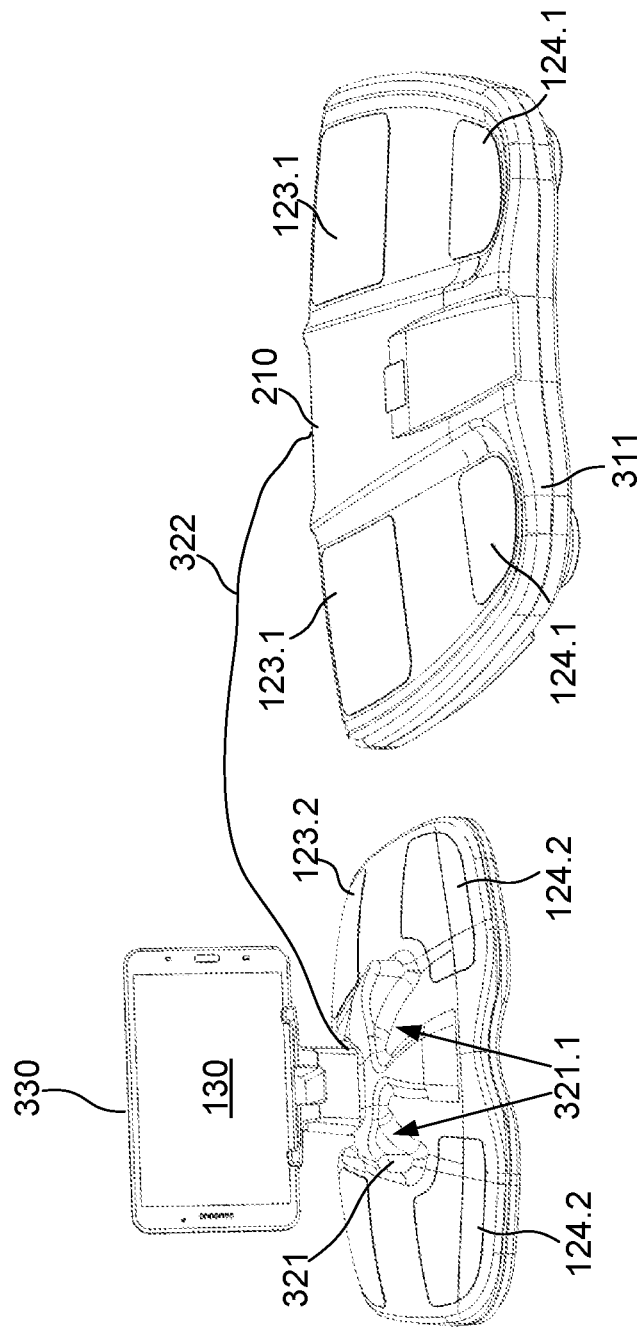
FIG. 3M is a rendering of an example of an impedance measuring apparatus incorporating the first and second housings of FIGS. 3A and 3G.
Figure 4A:
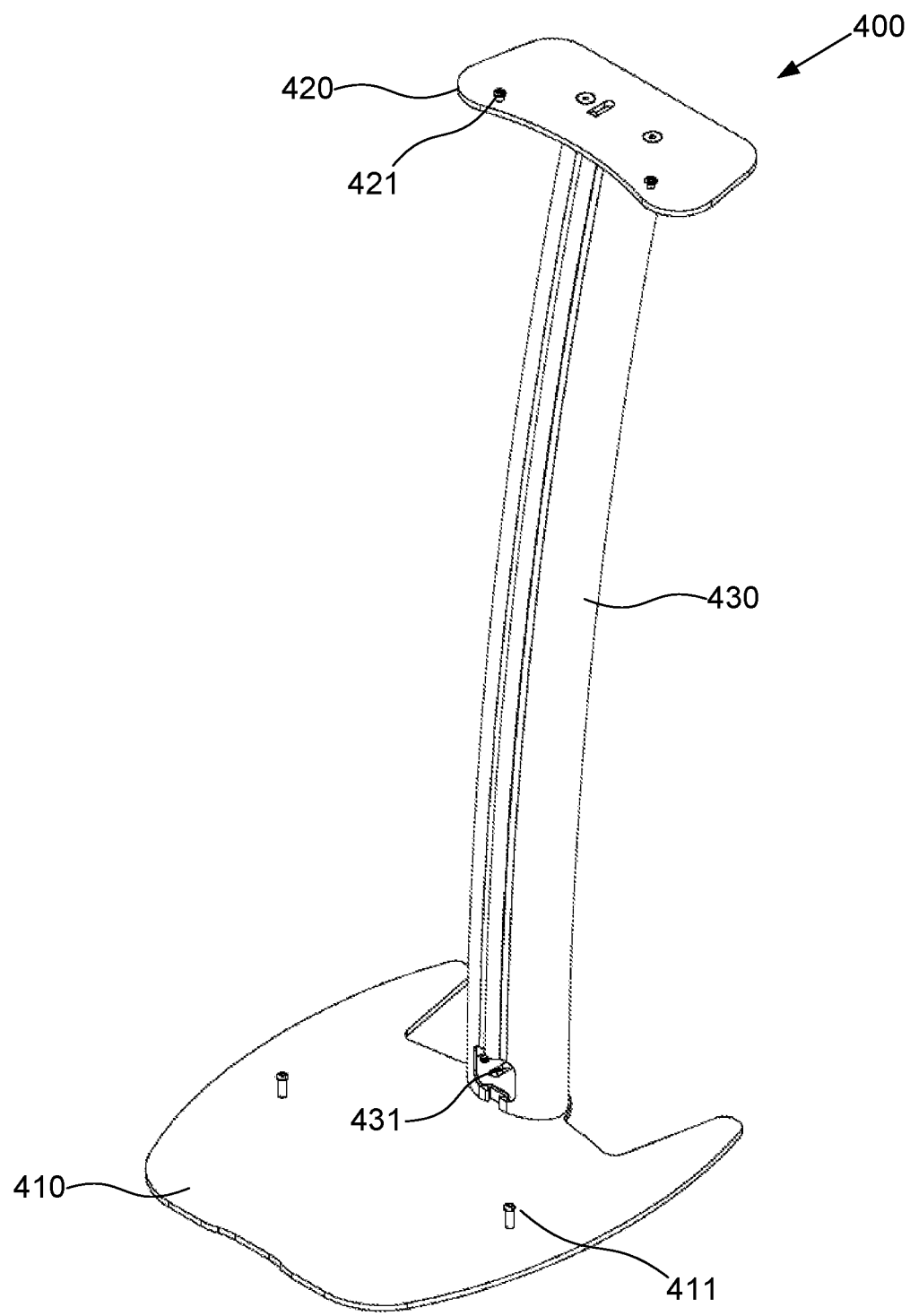
FIG. 4A is a schematic perspective view of a specific example of a stand.
Figure 4D:
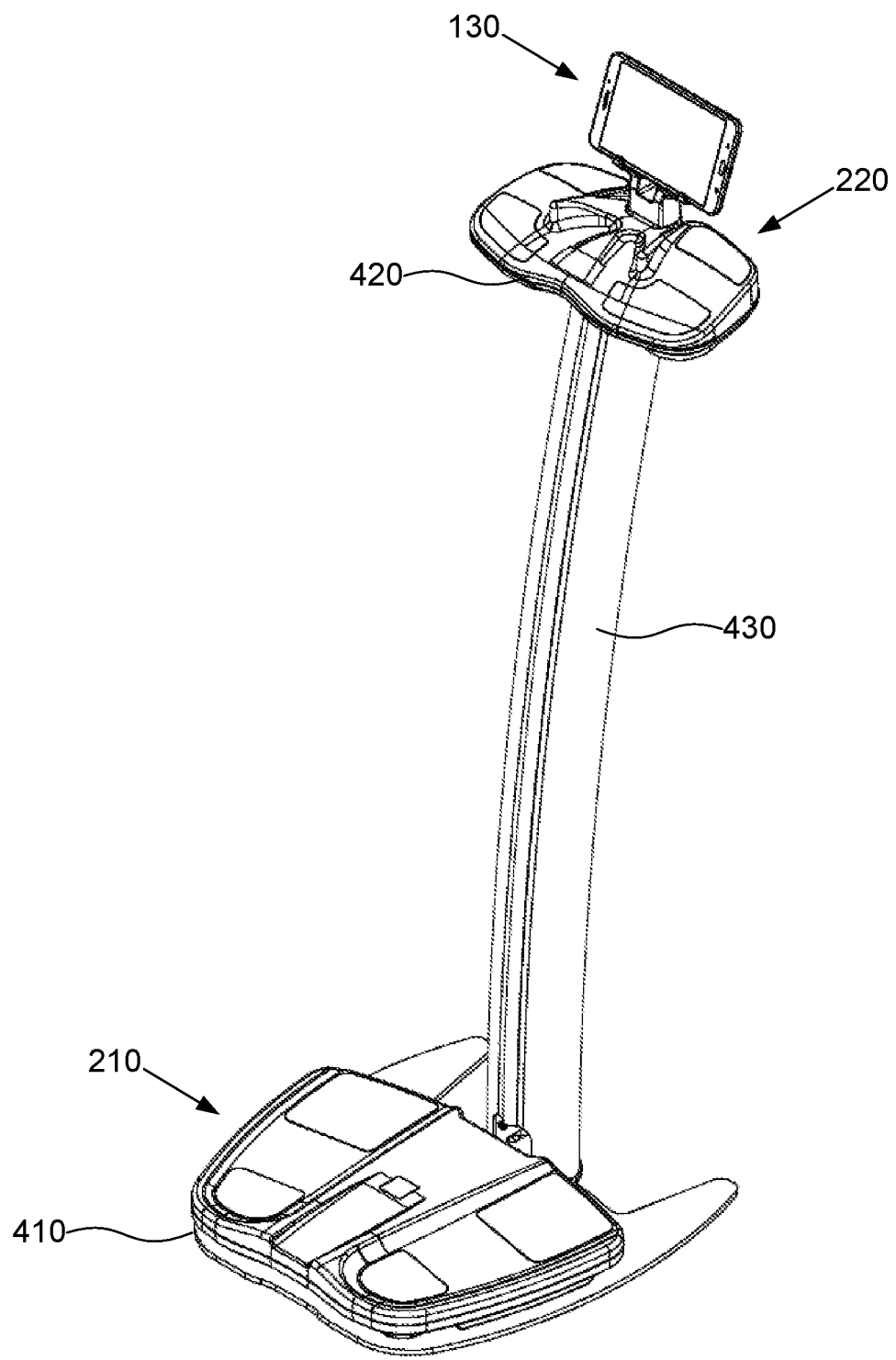
FIG. 4D is a schematic perspective view of an impedance measuring system including the stand of FIG. 4A and the first and second housings of FIGS. 3A and 3G.

An example of the physical construction of the measuring device is shown in FIG. 2.

In this example, the measuring device includes first and second housings 210, 220. The first housing 210 includes two spaced pairs of foot drive and sense electrodes 123.1, 124.1, which are typically made of spaced apart metal plates provided on an upper surface of the first housing 210, thereby forming footplates on which a user can stand. The second housing 220 includes two spaced pairs of hand drive and sense electrodes 123.2, 124.2 formed from spaced apart metal plates provided on an upper surface, thereby forming handplates on which a user can rest their hands.

This arrangement allows the unit to be used by having the user stand on the first housing, or alternatively sit on a chair, with their feet resting on the foot drive and sense electrodes. The user can then place their hands on the hand drive and sense electrodes on second housing, which can be supported by a desk or table in a seated arrangement, or by a stand or other support for a standing arrangement.

The use of two housing containing separate electrodes, therefore allows impedance measurements to be performed in a variety of circumstances, and in particular allows measurements to be performed in either seated or standing arrangements, which is important in ensuring the system can be used by individuals having restricted physical capabilities. Additionally, the use of metal plate electrodes provided in a housing allows the system to be readily used, and avoids the need for preparation, such as cleaning of tissue surfaces or removal of hair, to allow wet electrodes to be applied to the skin.

A number of further features will now be described with respect to FIGS. 3A to 3M, which show features of the first and second housings in more detail.

In this example, the first housing 210 is a cuboid having a generally rectangular side profile, with an isosceles trapezoidal shape in plan view, similar to a set of weighing scales. In one example, the housing is formed from moulded upper and lower portions 310.1, 310.2, which couple together to define an internal cavity 310.3, which in use contains required components mounted on a circuit board 315.

The electrodes 123.1, 124.1 are mounted on an upper surface of the upper housing 310.1, with the electrodes 123.1, 124.1 being made of a thin metallic plate, such as stainless steel or the like. The electrodes typically have downwardly facing tabs extending through openings in the housing 310.1, to thereby couple the electrodes to the housing and allow for electrical connection to the leads within the housing 210. In one example, the electrodes 123.1, 124.1 are slightly biased, for example by having a smaller spacing between openings in the housing than the distance between the tabs, so that the electrode curves slightly away from the housing 310.1 in a rest position. As a result, the electrodes bend when weight is applied until the electrodes 123.1, 124.1 rest against the housing 210, which in turn helps the electrodes 123.1, 124.1 conform to a shape of the subject's feet. This provides a greater degree of comfort and helps ensure good electrical contact.

To further assist with good electrical contact, the electrodes are sized and positioned to optimise consistent contact with the feet, whilst allowing a range of different feet sizes to be accommodated. In one example, the electrodes are spaced apart by at least one of at least 8 cm, at least 8.2 cm, at least 8.4 cm, up to 9 cm, up to 8.8 cm, up to 8.6 cm, between 8 cm and 9 cm, between 8.2 cm and 8.8 cm, between 8.4 cm and 8.6 cm and more typically approximately 8.5 cm. This enables a range of different foot sizes to be accommodated by the electrodes.

The foot drive electrode has a surface area that is at least one of at least 110 cm, at least 115 cm, at least 120 cm, at least 122 cm, up to 140 cm, up to 135 cm, up to 130 cm, up to 218 cm, between 110 cm$^2$ and 140 cm$^2$, between 115 cm$^2$ and 135 cm$^2$, between 120 cm$^2$ and 130 cm$^2$, between 122 cm$^2$ and 128 cm$^2$, approximately 125 cm$^2$ and more typically approximately 124.3 cm$^2$. The foot drive electrode has a square or parallelogram shape, with an approximately equal width and length to thereby accommodate different lengths and lateral positions for the ball of the subject's foot, which contacts the drive electrode in use, although other shapes and dimensions could be used.

The foot sense electrode has a surface area that is at least one of at least 35 cm, at least 40 cm, at least 45 cm, at least 50 cm, up to 70 cm, up to 65 cm, up to 60 cm, up to 55 cm, between 35 cm$^2$ and 70 cm$^2$, between 40 cm$^2$ and 65 cm$^2$, between 45 cm$^2$ and 60 cm$^2$, between 50 cm$^2$ and 55 cm$^2$, approximately 53 cm$^2$ and more typically approximately 52.6 cm$^2$. The foot sense electrode has a trapezoidal shape with curved edges, with a slightly greater width than length. This is because the position of the subject's heel is more constrained that the ball of the foot, by a guiding lip, as will be described in more detail below.

The above described dimensions ensure an approximately consistent surface area of contact between the subject's feet and the electrodes irrespective of minor variations in feet positioning, which helps ensure consistent measurements are obtained, allowing variations in measurements over time to be tracked more accurately. Additionally, the dimensions allow the apparatus to be used by subjects with a range in different feet sizes.

To further assist in controlling foot positioning, the first housing 210 includes a raised section 311, defining a lip extending at least partially around each pair of foot drive and sense electrodes to thereby guide positioning of a subject's foot relative to the foot drive and sense electrodes in use. In particular, the raised lip includes a rear portion 311.1 configured to engage at least a heel of the user, thereby helping guide the user in positioning their feet in a longitudinal direction, whilst the side portions 311.2 of the lip guide feet placement laterally. Guiding the subject's foot positioning in this manner can ensure good and more importantly, consistent contact between the feet and electrodes each time the system is used.

In this regard, it will be appreciated that whilst this will still allow for some minor variation in positioning between different subjects, for example due to different feet sizes, this helps ensure that any given subject's feet are provided at a consistent position relative to the drive and sense electrodes each time the system is used. This provides reproducible positioning, which in turn reduces variations between successive measurements that could be caused by changes in foot position. Consequently, this helps ensure the system can be used for more reliable longitudinal measurements.

The first housing, and in particular the lower portion 310.2 includes measuring device feet 312 that support the first housing spaced from a surface, with supporting ridges 313 extending downwardly and longitudinally along opposing edges of the lower portion. The supporting ridges 313 provide additional stability, and in particular can engage the floor in the event the apparatus becomes unbalanced, thereby preventing the apparatus from tipping over.

The measuring device feet 312 engage load cells mounted within the first housing 210, allowing the measuring device processor 112 to determine a weight of a subject standing on the first housing 210. In order to ensure accurate weight measurements are captured, the housing 210 contains a rigid internal plate 314, typically made of steel or the like. The upper housing portion 310.1 engages the plate, so that weight of the user is transmitted to the plate 314.

Each of the measuring device feet 312 include a foot assembly having a load cell mounting 312.1 in the form of a cylindrical body attached to an extending downwardly from an underside of the plate 314, and a foot member 312.2 at least partially positioned within and movable within the load cell mounting 312.1. A load cell 312.3 is coupled to the load cell mounting 312.1 and the foot member 312.2, via respective screws 312.4, so the load cell deforms under relative movement of the load cell mounting 312.1 and foot member 312.2. In use, when a user stands on the housing 210, the load is transmitted via the rigid plate 314 and the load cell mountings 312.1 to the load cells 312.3, allowing respective load signals to be generated, which can in turn be used to calculate the subject's weight.

The circuitry provided on the circuit board 315, will typically include signal generators and sensors for the foot drive and sense electrodes. Additionally, the circuitry can include power systems, for example for voltage conversion or the like. As a result, the board 315 tends to have a slightly elevated temperature, which in turn warms the electrodes, making these more comfortable to stand on.

The second housing 220 is a cuboid having a generally triangular side profile, with an isosceles trapezoidal shape in plan view. In one example, the housing is formed from moulded upper and lower portions 320.1, 320.2, which couple together to define an internal cavity 320.3, which in use contains required components mounted on a circuit board (not shown).

The electrodes 123.2, 124.2 are mounted on an upper surface of the upper housing 320.1. The electrodes 123.2, 124.2 are typically made of a thin metallic plate, such as a stainless steel plate, and having tabs extending through openings in the housing 320.1, to thereby couple the electrodes to the housing and allow for electrical connection to the leads. Again, the electrodes may be raised from the housing 320.1 in a rest position, so that the electrodes bend when weight is applied, to help the electrodes conform to a shape of the subject's hands. This provides a greater degree of comfort and helps ensure good electrical contact.

Additionally, an upper surface of the second housing is shaped to at least partially conform to a shape of a subject's hands. In particular, the second housing has a curved upper surface, to help the subject rest their hands on the surface even if they are unable to lay their hands out completely flatly, for example due to arthritis, or the like. In one example, the hand sense electrode 124.2 contact the subject's palms, with the drive electrodes 123.2 contacting the fingers. In this instance, as subject's are more likely to have difficulty straightening their fingers, the radius of curvature of the hand drive electrode is different to, and typically less than a radius of curvature of the hand sense electrode, so the hand drive electrode is more curved.

In one example, a radius of curvature of the hand drive electrode is at least one of at least 100 mm, at least 110 mm, at least 115 mm, at least 118 mm, up to 150 mm, up to 130 mm, up to 125 mm, up to 122 mm, between 100 mm and 150 mm, between 110 mm and 130 mm, between 115 mm and 125 mm, between 118 mm and 122 mm, approximately 120 mm and more typically approximately 119.5 mm A radius of curvature of the hand sense electrode is at least one of at least 180 mm, at least 200 mm, at least 210 mm, at least 215 mm, up to 260 mm, up to 240 mm, up to 230 mm, up to 225 mm, between 180 mm and 260 mm, between 200 mm and 240 mm, between 210 mm and 230 mm, between 215 mm and 225 mm, approximately 220 mm and more typically approximately 218 mm A region between the drive and sense electrodes typically has an intermediate curvature.

To further assist good electrical contact, over a range of different hand sizes, the hand drive and sense electrodes in each pair are typically spaced apart by at least one of at least 3 cm, at least 3.2 cm, at least 3.4 cm, up to 4 cm, up to 3.8 cm, up to 3.6 cm, between 3 cm and 4 cm, between 3.2 cm and 3.8 cm, between 3.4 cm and 3.6 cm and more typically approximately 3.5 cm.

To further ensure good electrical contact, and in particular a consistent contact surface area irrespective of exact positioning, the hand drive electrode typically has a surface area that is at least one of at least 35 cm, at least 38 cm, at least 40 cm, at least 41 cm, up to 50 cm, up to 45 cm, up to 43 cm, up to 42 cm, between 35 $cm^2$ and 50 $cm^2$, between 38 $cm^2$ and 45 $cm^2$, between 40 $cm^2$ and 43 $cm^2$, between 41 $cm^2$ and 42 $cm^2$, approximately 41 $cm^2$ and more typically approximately 41.4 $cm^2$. The drive electrode has a curved generally rectangular shape and is wider than long to accommodate lateral movement and splaying of the fingers.

Similarly, the hand sense electrode has a surface area that is at least one of at least 35 cm, at least 40 cm, at least 45 cm, at least 46 cm, up to 55 cm, up to 50 cm, up to 49 cm, up to 48 cm, between 35 $cm^2$ and 55 $cm^2$, between 40 $cm^2$ and 50 $cm^2$, between 45 $cm^2$ and 49 $cm^2$, between 46 $cm^2$ and 48 $cm^2$, approximately 47 $cm^2$ and more typically approximately 46.8 $cm^2$. The hand sense electrode is rectangular, with a cut-out section that accommodates the guide ridge discussed in more detail below. The hand sense electrode is typically twice as wide as it is long to accommodate the position of the thumb as it extends outwardly around the guide ridge.

Additionally, a guide is provided to assist the subject in positioning their hands. In one example, this is achieved by having a raised portion 321 positioned between each pair of hand drive and sense electrodes, the raised portion defining thumb recesses 321.1 to thereby guide positioning of a subject's thumbs, with the crook of the thumb engaging the raised portion, and hence hands relative to each pair of hand drive and sense electrodes in use. In particular, the raised portion includes two ridges 321.2, each ridge extending towards a respective hand sense electrodes 124.2, and terminating level with an edge of the sense electrode closest to the drive electrode, and being adapted to be positioned between a subject's thumb and forefinger, to thereby guide subject hand placement.

The second housing can also include a recessed portion 326 along one edge of an underside surface of the second housing, allowing a user to insert their fingers between the second housing and a support surface, to thereby more easily lift the second housing. Connector ports in a rear face of the first and second housing, for example to receive a lead 322 that attaches to the first housing 210, can also positioned beneath an overhang, to thereby reduce ingress of water drops into the connectors. Finally, the second housing can accommodate a USB port for charging a tablet or other processing device when coupled thereto.

In this regard, the second housing can include a processing system mounting 327 that in use receives a support 330, for supporting a processing system, such as the client device 130, and in particular a tablet, smartphone or other similar client device. In this regard, the mounting 327 can include a rectangular plug extending upwardly from an upper surface of the housing, allowing a mounting stem 331 of the support 330 to be seated thereon. The support 330 further includes as frame including a back surface 332, and lip 333, on which the client device rests, with retaining lugs 334 extending upwardly from a front of the lip to prevent the client device slipping therefrom. This allows a tablet or other processing device to be suitably integrated into the connectivity module.

In one example, the mounting step 331 incorporates a pivoting arrangement, allowing the client device to be rotated about a substantially vertical axis, so that the client device 130 can face towards or away from the subject, so that this can be used to allow the subject or another user, such an operator or clinician, to control the measurement process and view results. Additionally, the pivoting arrangement can be used to pivot the frame about a horizontal axis, allowing the client device 130 to be tilted, allowing this to be more easily viewed by the subject, depending on the subject's height.

In one example, the system can be used in conjunction with a stand and an example of this will now be described with reference to FIGS. 4A to 4F.

In this example, the stand 400 includes a base 410 that supports the first housing 210, a platform 420 that supports the second housing 220, and a leg 430 coupled to the base 410 and platform 420 to support the platform 420 relative to the base 410. The stand 400 can be made of any suitable material, and in one example, includes metal plates, such as aluminium or steel plates, forming the base 410 and platform 420, with the leg being made of extruded aluminium or the like.

The base and platform typically include mounting lugs 411, 421 which engage keyhole mountings provided in an underside of the first and second housings, allowing the first and second housings to be removably mounted to the base and platform respectively.

The leg typically includes an internal cavity that receives the connector lead 322, allowing this to pass through the cavity via an opening 431, so this is hidden from view in use.

The leg 430 is typically curved so that a centre of the platform 420 is offset from a centre of the base 410 in a longitudinal direction, so that as the subject stands on the first housing the second housing is provided in front of the subject. The platform is typically spaced from the base by a vertical distance of at least one of at least 100 cm, at least 103 cm, at least 104 cm, at least 105 cm, up to 110 cm, up to 108 cm, up to 107 cm, up to 106 cm, between 100 cm and 110 cm, between 103 cm and 108 cm, between 104 cm and 107 cm, between 105 cm and 106 cm, approximately 105.5 cm and more typically 105.4 cm. The use of a fixed relative position between the base and platform means that the subject is in the same physical position each time a measurement is performed, which helps ensure that changes in readings are as a result of changes in fluid levels and not simply due to redistribution of fluids caused by a change in subject position. It will be appreciated that this allows consistent measurements to be performed on a single subject between different pieces of equipment, allowing measurements to be compared even if different measuring devices are used.

The stand can incorporate lighting, such as LEDs mounted in the platform, base or leg, for aesthetic appearances.

Figure 5A:
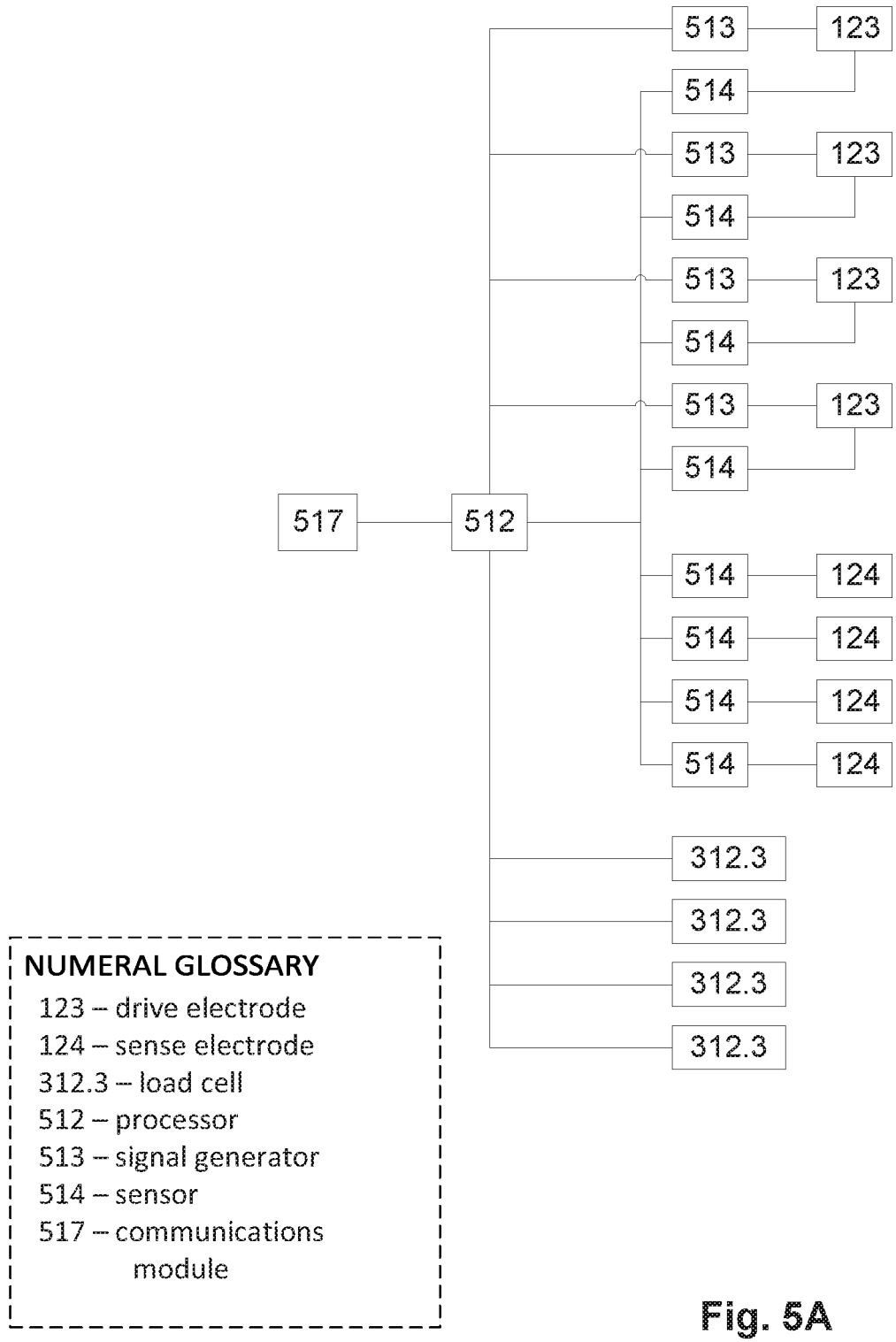
FIG. 5A is a schematic diagram of an example of a measuring device sensor configuration.

In the above example, the apparatus includes four drive electrodes and four sense electrodes. Accordingly, in one example, a four channel system can be provided, and an example of this will now be described with reference to FIG. 5A.

In this example, the system includes the measuring device processor 512, which is in turn connected to signal four generators 513, allowing drive signals to be applied to each of the drive electrodes 123. Eight sensors 514 are provided coupled to each of the sense electrodes 124, as well as the drive electrodes 123, allowing the drive electrodes to be used for sensing, for example when sensing ECG or other body signals.

The measuring device processor 512 is also typically connected to the load cells 312.3, allowing weight measurements to be performed, as well as a communications module 517 for communication with the client device 130.

In use, the measuring device processor selectively controls the four signal generators 513 and four sensors 514 coupled to the sense electrodes 124, to perform a sequence of impedance measurements, including segmental impedance measurements and/or whole of body impedance measurements. In this regard, example electrode arrangements are shown in FIGS. 5B to 5D, with active electrodes being shown filled and inactive electrodes shown as unfilled circles. In these examples, the configuration of FIG. 5B can be used for whole body measurements, whereas the arrangements of FIGS. 5C and 5D are used for the right arm and leg respectively. It will be appreciated that other configurations can be used to measure other limbs, torso, or the like.

The manner in which impedance measurements are performed will now be described in more detail. In particular, the measuring device processor 512 is adapted to generate control signals, which cause the signal generators 513 to generate one or more alternating signals, such as voltage or current signals of an appropriate waveform, which can be applied to a subject S, via the first electrodes 123. The measuring device processor 512 also receives an indication of measured response signals from the sense electrodes 124 and sensors 514, processing these and an indication of the applied drive signals to determine impedance values. It will be appreciated that the measuring device processor 512 may be any form of electronic processing device capable of performing appropriate control, and could include an FPGA (field programmable gate array), or a combination of a programmed computer system and specialised hardware, or the like.

The signal generators 513 could be of any appropriate form, but will typically include digital to analogue converters (DACs) for converting digital signals from the processing device to analogue signals, which are amplified to generate the required drive signals, whilst the sensors 514 typically includes one or more amplifiers for amplifying sensed response signals and analogue to digital converters (ADCs) to digitise the analogue response signals and providing digitised response signals to the processing device.

The nature of the alternating drive signal will vary depending on the nature of the measuring device and the subsequent analysis being performed. For example, the system can use Bioimpedance Analysis (BIA) in which a single low frequency signal is injected into the subject S, with the measured impedance being used directly in the determination of biological parameters. In one example, the applied signal has a relatively low frequency, such as below 100 kHz, more typically below 50 kHz and more preferably below 10 kHz. In this instance, such low frequency signals can be used as an estimate of the impedance at zero applied frequency, commonly referred to as the impedance parameter value $R_0$, which is in turn indicative of extracellular fluid levels.

Alternatively, the applied signal can have a relatively high frequency, such as above 200 kHz, and more typically above 500 kHz, or 1000 kHz. In this instance, such high frequency signals can be used as an estimate of the impedance at infinite applied frequency, commonly referred to as the impedance parameter value $R_\infty$, which is in turn indicative of a combination of the extracellular and intracellular fluid levels, as will be described in more detail below.

Alternatively and/or additionally, the system can use Bioimpedance Spectroscopy (BIS) in which impedance measurements are performed at each of a number of frequencies ranging from very low frequencies (1 kHz and more typically 3 kHz) to higher frequencies (1000 kHz), and can use as many as 256 or more different frequencies within this range. Such measurements can be performed by applying a signal which is a superposition of plurality of frequencies simultaneously, or a number of alternating signals at different frequencies sequentially, depending on the preferred implementation. The frequency or frequency range of the applied signals may also depend on the analysis being performed.

When impedance measurements are made at multiple frequencies, these can be used to derive one or more impedance parameter values, such as values of $R_0$, $Z_c$, $R_\infty$, which correspond to the impedance at zero, characteristic and infinite frequencies. These can in turn be used to determine information regarding both intracellular and extracellular fluid levels, as will be described in more detail below.

A further alternative is for the system to use Multiple Frequency Bioimpedance Analysis (MFBIA) in which multiple signals, each having a respective frequency are injected into the subject S, with the measured impedances being used in the assessment of fluid levels. In one example, four frequencies can be used, with the resulting impedance measurements at each frequency being used to derive impedance parameter values, for example by fitting the measured impedance values to a Cole model, as will be described in more detail below. Alternatively, the impedance measurements at each frequency may be used individually or in combination.

Thus, the measuring device 110 may either apply an alternating signal at a single frequency, at a plurality of frequencies simultaneously, or a number of alternating signals at different frequencies sequentially, depending on the preferred implementation. The frequency or frequency range of the applied signals may also depend on the analysis being performed.

In one example, the applied signal is generated by a voltage generator, which applies an alternating voltage to the subject S, although alternatively current signals may be applied. In one example, the voltage source is typically symmetrically arranged, with two signal generators 313 being independently controllable, to allow the signal voltage across the subject to be varied, for example to minimise a common mode signal and hence substantially eliminate any imbalance as described in copending patent application number WO2009059351.

As the drive signals are applied to the subject, the sensors 514 then determines the response signal in the form of the voltage across or current through the subject S, using sense electrodes 124. Thus, a voltage difference and/or current is measured between the sense electrodes 124. In one example, a voltage is measured differentially, meaning that two sensors 514 are used, with each sensor 514 being used to measure the voltage at each sense electrode 124 and therefore need only measure half of the voltage as compared to a single ended system. Digitised response signals are then provided to the measuring device processor 512, which determines an indication of the applied drive signal and measured response signals, and optionally uses this information to determine measured impedances.

In this regard, the response signal will be a superposition of voltages generated by the human body, such as the ECG (electrocardiogram), voltages generated by the applied signal, and other signals caused by environmental electromagnetic interference. Accordingly, filtering or other suitable analysis may be employed to remove unwanted components.

The acquired signal is typically demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a signal processing technique such as multiplying the measured signal with a reference sine wave and cosine wave derived from the signal generator, or with measured sine and cosine waves, and integrating over a whole number of cycles. This process, known variously as quadrature demodulation or synchronous detection, rejects all uncorrelated or asynchronous signals and significantly reduces random noise. Other suitable digital and analogue demodulation techniques will be known to persons skilled in the field.

In the case of BIS, impedance or admittance measurements are determined from the signals at each frequency by comparing the recorded voltage and the current through the subject. The demodulation algorithm can then produce amplitude and phase signals at each frequency, allowing an impedance value at each frequency to be determined.

Whilst the measured impedance can be used directly, in one example, the measured impedance is used to derive an impedance parameter, such as an impedance (resistance) at zero frequency, $R_0$, which equals the extracellular resistance $R_e$, or the impedance at a theoretical infinite frequency $R_\infty$, which can be used with $R_0$ to derive an intracellular resistance $R_i$, as well as other impedance parameters. The impedance parameters may be determined in any one of a number of manners such as by:

estimating values based on impedance measurements performed at selected respective frequencies, solving simultaneous equations based on the impedance values determined at different frequencies;

using iterative mathematical techniques;

extrapolation from a plot of resistance against reactance for impedance measurements at a plurality of frequencies; and, performing a function fitting technique, such as the use of a polynomial function.

In one example, the frequencies used are in the range 0 kHz to 1000 kHz, and in one specific example, four measurements are recorded at frequencies of 25 kHz, 50 kHz, 100 kHz, and 200 kHz, although any suitable measurement frequencies can be used.

A further alternative for determining impedance parameter values is to perform impedance measurements at a single frequency, and use these as an estimate of the parameter values. In this instance, measurements performed at a single low frequency (typically less than 50 kHz) can be used to estimate $R_0$, measurements at a single high frequency (typically more than 100 kHz) can be used to estimate $R_\infty$, allowing a value of $R_i$ to be determined.

The above described equivalent circuit models the resistivity as a constant value and does not therefore accurately reflect the impedance response of a subject, and in particular does not accurately model the change in orientation of the erythrocytes in the subject's blood stream, or other relaxation effects. To more successfully model the electrical conductivity of the human body, an improved CPE based model may alternatively be used.

When performing measurements of cardiac and/or respiratory parameters, the system is typically used passively, with signals being measured via the sense electrodes 124 and optionally also via the drive electrodes 123. The detected signals are a superposition of voltages generated by the human body, and will include cardiac and respiratory components, which can typically be isolated through suitable filtering, for example 1-40 Hz for cardiac signals and below 1 Hz for respiratory signals.

Figure 6:
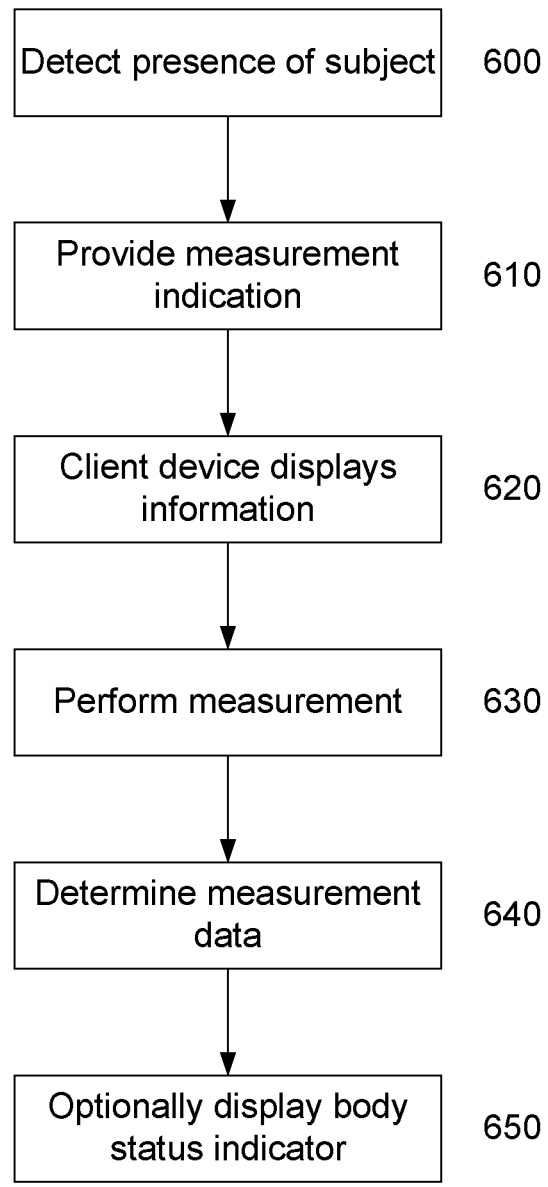
FIG. 6 is a flow chart of an example of an impedance measuring process.

A typical measurement process using the above described apparatus will now be described with respect to FIG. 6.

In this example, at step 600 the system acts to detect the presence of a subject. This can be achieved in any suitable manner, and could involve detecting the weight of a subject standing on the first housing, contact with the drive or sense electrodes, or activation of a suitable application on the client device 130, with this being communicated to the measuring device.

At step 610, the measuring device processor provides a measurement indication to the client device, thereby allowing the client device 130 to display relevant information to the subject at step 620. The information can include any information regarding the measurement process, including an indication of the measurement being performed, a time to completion, instructions to the subject, for example asking the subject to stand still, or the like. This allows the subject to prepare for the measurement, and ensure they are positioned correctly for the relevant measurement being performed. The interface could also display information regarding the measurements, including results, previous measurements or the like, as well as questions requesting further information from the user, such as asking the user questions relating to current symptoms, or the like.

At step 630 the measuring device processor 512 performs a measurement procedure. Typically multiple measurement procedures are performed in sequence, for example by performing a weight measurement, impedance measurement and then measurement of cardiac and/or respiratory parameters. It will be appreciated that the system may be configured to always perform each of these, or alternatively may be configured to only perform selected ones of the procedures depending on the preferred implementation and/or current settings.

As the measurement process is completed, the measuring device processor determines measurement data at step 640, which can include raw data, such as values of the magnitude and/or phase of measured signals, processed values, such as impedance values, or the like. The measurement data is provided to the client device 130, at step 650, allowing client device to display a body status indicator indicative of a body status of the subject.

The nature of the body status indicator will vary depending on the preferred implementation and could include a simple indication of measured parameter values, such as impedance values, a heart rate, respiration rate, or the like. Alternatively, the body status indicator could include values derived from the measured parameter values, such as an indication of body composition parameters, an indication of relative water levels, measurement of a disease state or the like. The body status indicator could be based on current measurements alone, or could take into account prior measurements, for example, examining variations in fluid levels over time.

Accordingly, the above described process can detect the presence of the subject and then trigger the measurement process, including an impedance measurement process, and optionally other measurement processes, with information being presented to the subject via the client device.

A number of further features will now be described.

In one example, the body status indicators can include, but are not limited to any one or more of:

Body Composition
Dry Lean Mass
Lean Body Mass
Skeletal Muscle Mass
Segmental Lean Analysis
Body Fat Mass
Segmental Fat Analysis
BMI (Body Mass Index)
Percent Body Fat
Visceral Fat Area
Visceral Fat Level
Total Body Water
Intracellular Water
Extracellular Water
ECW/TBW
Segmental Body Water
Segmental ECW/TBW
Segmental ICW Analysis
Segmental ECW Analysis
Body-Fat-LBM Control
BMR (Basal Metabolic Rate)
Leg Lean Mass
TBW/LBM
Whole Body Phase Angle
Segmental Phase Angle
Reactance
Impedance of Each Segment per frequency
Body Water Composition History In one example, the measuring device processor 512 provides a measurement indication to the client device, the measurement indication being indicative of a measurement being performed. Thus, the measuring device processor 512 can determine a presence of a subject in accordance with signals from at least one of the load cells and the at least one sensor, commence at least one measurement procedure and provide the measurement indication to the client device. The client device is responsive to the measurement indication to display information to the subject including information regarding the measurement process, measured signals, a body parameter value, a body status indicator, instructions to the subject and a question for the subject. This allows the system to automatically commence measurements and display relevant information to the subject, so the subject can see the measurement is being performed, and allowing them to take appropriate action, such as standing in a correct position.

In one example, the measuring device processor detects when a subject is standing on the foot unit in accordance with signals from at least one of the load cells and causes a weight measurement procedure to be performed using signals from the load cells. Thus, this can be used to automatically trigger a weight measurement process when the subject stands on the first housing. Similarly, the measuring device processor detects when a subject's hands and feet are positioned in contact with the hand and feet electrodes in accordance with signals from the at least one sensor and cause a measurement procedure to be performed including at least one of an impedance measurement procedure, a cardiac measurement procedure and a respiration measurement procedure. Thus, a suitable measurement can be automatically performed depending on the subject's interaction with the measuring device, with impedance or other measurements only being performed when the subject's hands and feet are in contact with the respective electrodes, whilst weight measurements are performed when the subject's hands are not in contact with the hand sense/drive electrodes.

Thus, in one example, the measuring device processor detects when a subject is standing on the foot unit in accordance with signals from at least one of the load cells, provides weight measurement indication to the client device, the client device being responsive to the weight measurement indication to instruct the subject to stand for a weight measurement, before the weight measurement is performed. Following this, the measuring device processor provides a body measurement indication to the client device, the client device being responsive to the body measurement indication to instruct the subject to place their feet and hands on the respective electrodes, detects when a subject's hands and feet are positioned in contact with the hand and feet electrodes in accordance with signals from the at least one sensor and commences an impedance measurement procedure, a cardiac measurement procedure or respiration measurement procedure. Following this results can be displayed to the user. Thus, this allows the subject to be informed throughout the measurement process, whilst ensuring the process only progresses once the subject is correctly positioned, thereby ensuring accuracy of the measurements.

Figure 7:
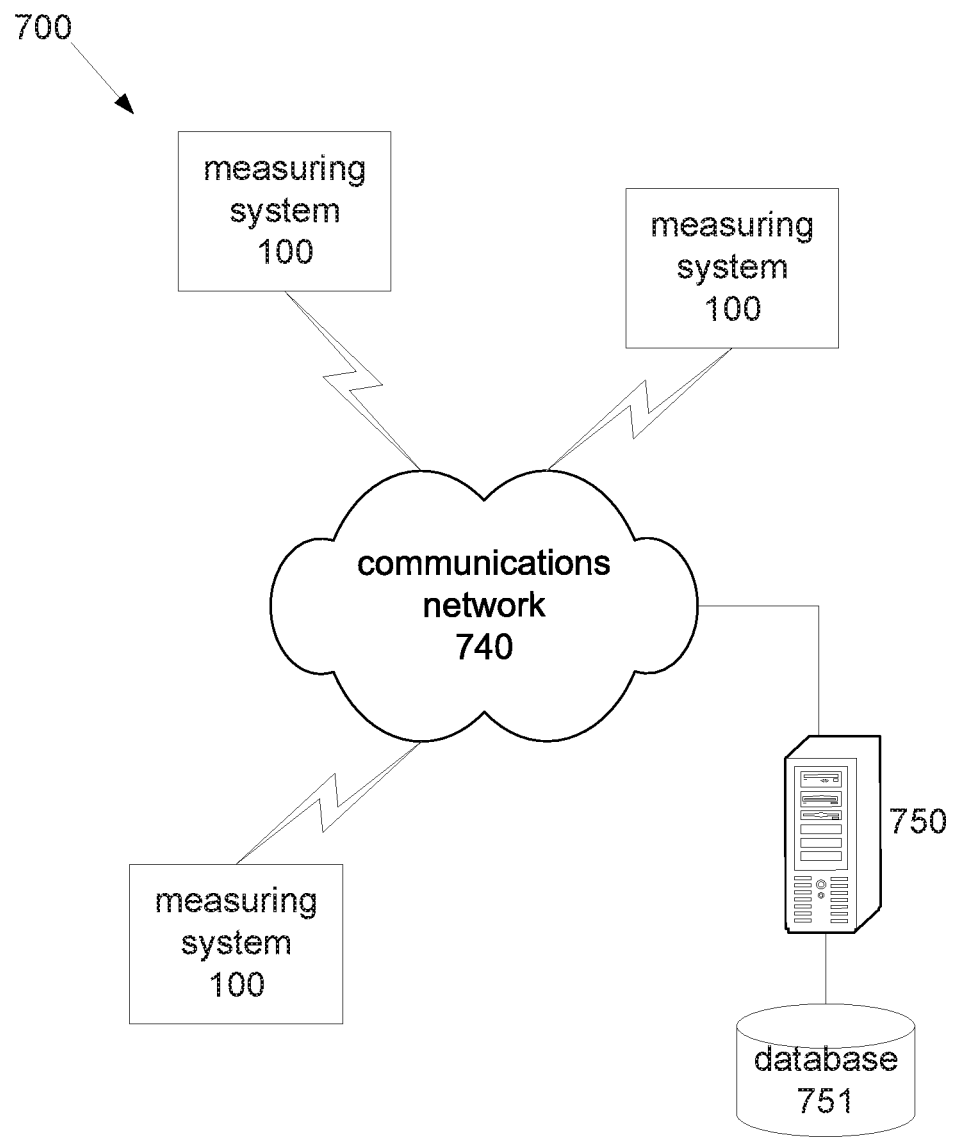
FIG. 7 is a schematic diagram of a distributed system architecture.

A specific example system will now be described in more detail with reference to FIGS. 7 to 9.

In this example, the system 700 includes a number of measuring systems 100 coupled via a communications network 740 to one or more processing devices, such as a server 750, which may in turn be coupled to a database 751. This arrangement allows subject data to be collected by the measurement systems 100 and provided to the server 750 for storage and optional analysis. Collected subject data may be stored in the database 751 together with other information, such as body state indicators, allowing this information to be remotely accessed and viewed by authorised users, such as clinicians, or the like.

In the above arrangement, the communications network 740 can be of any appropriate form, such as the Internet and/or a number of local area networks (LANs) and provides connectivity between the measuring systems 100 and the server 750. It will however be appreciated that this configuration is for the purpose of example only, and in practice the measuring systems 100 and server 750 can communicate via any appropriate mechanism, such as via wired or wireless connections, including, but not limited to mobile networks, private networks, such as an 802.11 networks, the Internet, LANs, WANs, or the like, as well as via direct or point-to-point connections, such as Bluetooth, or the like.

Figure 8:
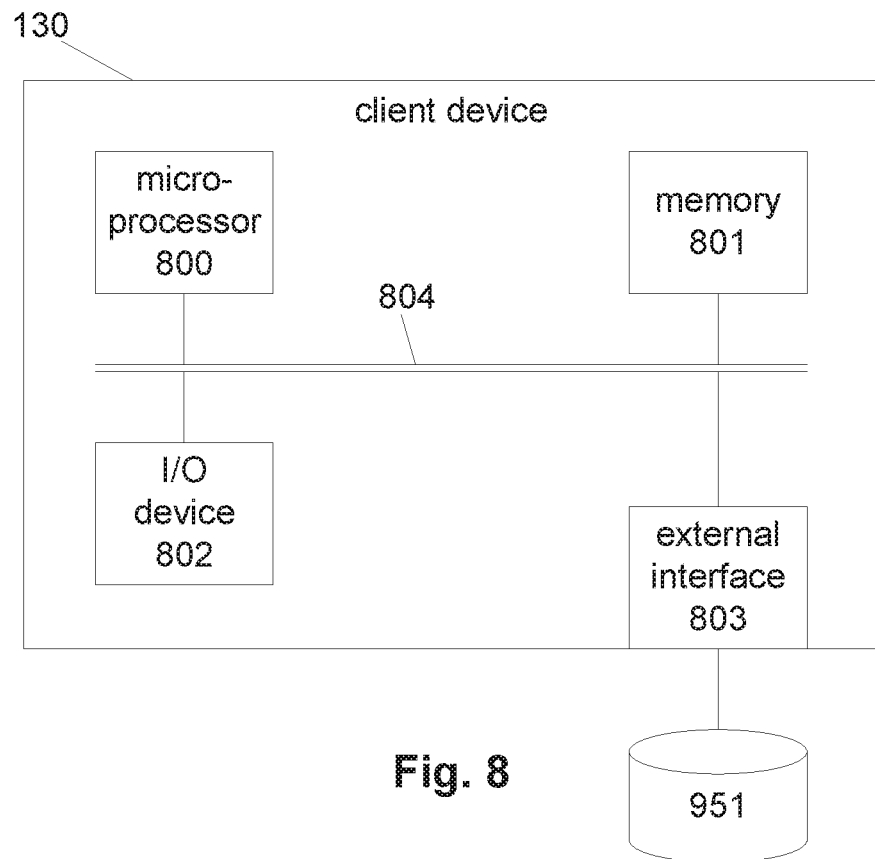
FIG. 8 is a schematic diagram of an example of a processing system.

Accordingly, it will be appreciated that the client device 130 can be of any appropriate form and one example is shown in FIG. 8.

In this example, the client device 130 includes at least one microprocessor 800, a memory 801, an input/output device 802, such as a keyboard and/or display, and an external interface 803, interconnected via a bus 804 as shown. The external interface 803 can be utilised for connecting the client device 130 to peripheral devices, such as the communications networks 740, databases, other storage devices, or the like. Although a single external interface 803 is shown, this is for the purpose of example only, and in practice multiple interfaces using various methods (eg. Ethernet, serial, USB, wireless or the like) may be provided.

In use, the microprocessor 800 executes instructions in the form of applications software stored in the memory 801 to allow communication with the server 750, for example to allow subject data to be provided to the sever, or the like.

Accordingly, it will be appreciated that the client device 130 may be formed from any suitable processing system, such as a suitably programmed PC, Internet terminal, laptop, or hand-held PC, and in one preferred example is either a tablet, or smart phone, or the like. Thus, in one example, the client device 130 is a standard processing system such as an Intel Architecture based processing system, which executes software applications stored on non-volatile (e.g., hard disk) storage, although this is not essential. However, it will also be understood that the client devices 130 can be any electronic processing device such as a microprocessor, microchip processor, logic gate configuration, firmware optionally associated with implementing logic such as an FPGA (Field Programmable Gate Array), or any other electronic device, system or arrangement.

Figure 9:
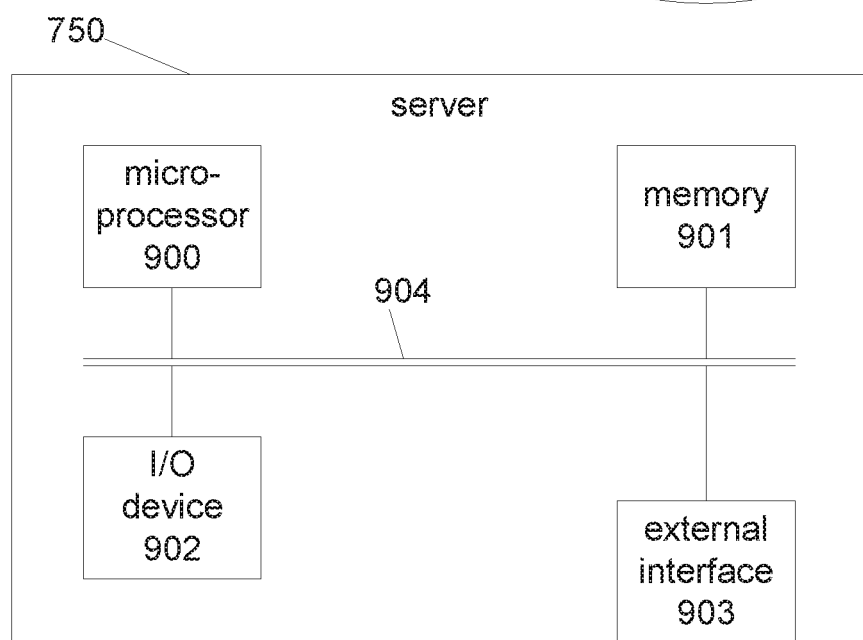
FIG. 9 is a schematic diagram of an example of a client device.

An example of a suitable server 750 is shown in FIG. 9. In this example, the server includes at least one microprocessor 900, a memory 901, an optional input/output device 902, such as a keyboard and/or display, and an external interface 903, interconnected via a bus 904 as shown. In this example the external interface 903 can be utilised for connecting the server 750 to peripheral devices, such as the communications networks 740, databases 751, other storage devices, or the like. Although a single external interface 903 is shown, this is for the purpose of example only, and in practice multiple interfaces using various methods (eg. Ethernet, serial, USB, wireless or the like) may be provided.

In use, the microprocessor 900 executes instructions in the form of applications software stored in the memory 901 to allow the required processes to be performed, including communicating with the client devices 130, and optionally receiving, analysing and/or displaying results of impedance measurements. The applications software may include one or more software modules, and may be executed in a suitable execution environment, such as an operating system environment, or the like.

Accordingly, it will be appreciated that the server 750 may be formed from any suitable processing system, such as a suitably programmed client device, PC, web server, network server, or the like. In one particular example, the server 750 is a standard processing system such as an Intel Architecture based processing system, which executes software applications stored on non-volatile (e.g., hard disk) storage, although this is not essential. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement. Accordingly, whilst the term server is used, this is for the purpose of example only and is not intended to be limiting.

Whilst the server 750 is a shown as a single entity, it will be appreciated that the server 750 can be distributed over a number of geographically separate locations, for example by using processing systems and/or databases 751 that are provided as part of a cloud based environment. Thus, the above described arrangement is not essential and other suitable configurations could be used.

Figure 10A:
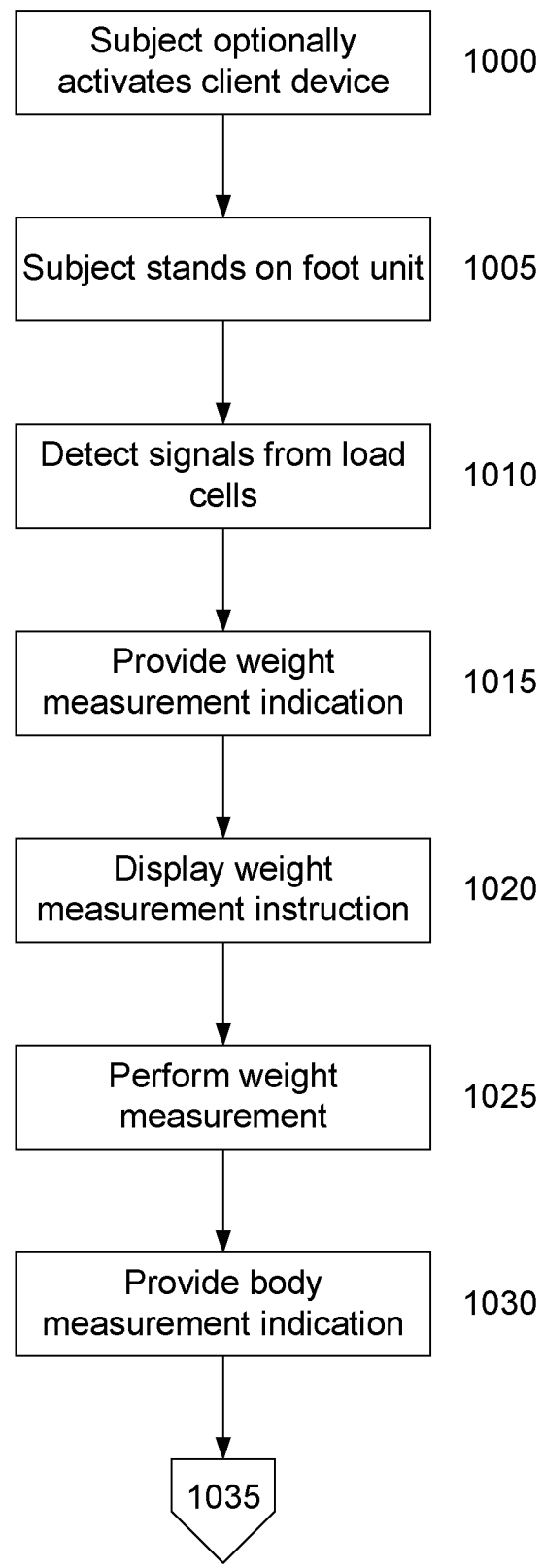
FIGS. 10A to 10C are a flow chart of an example of a measurement process.
Figure 10B:
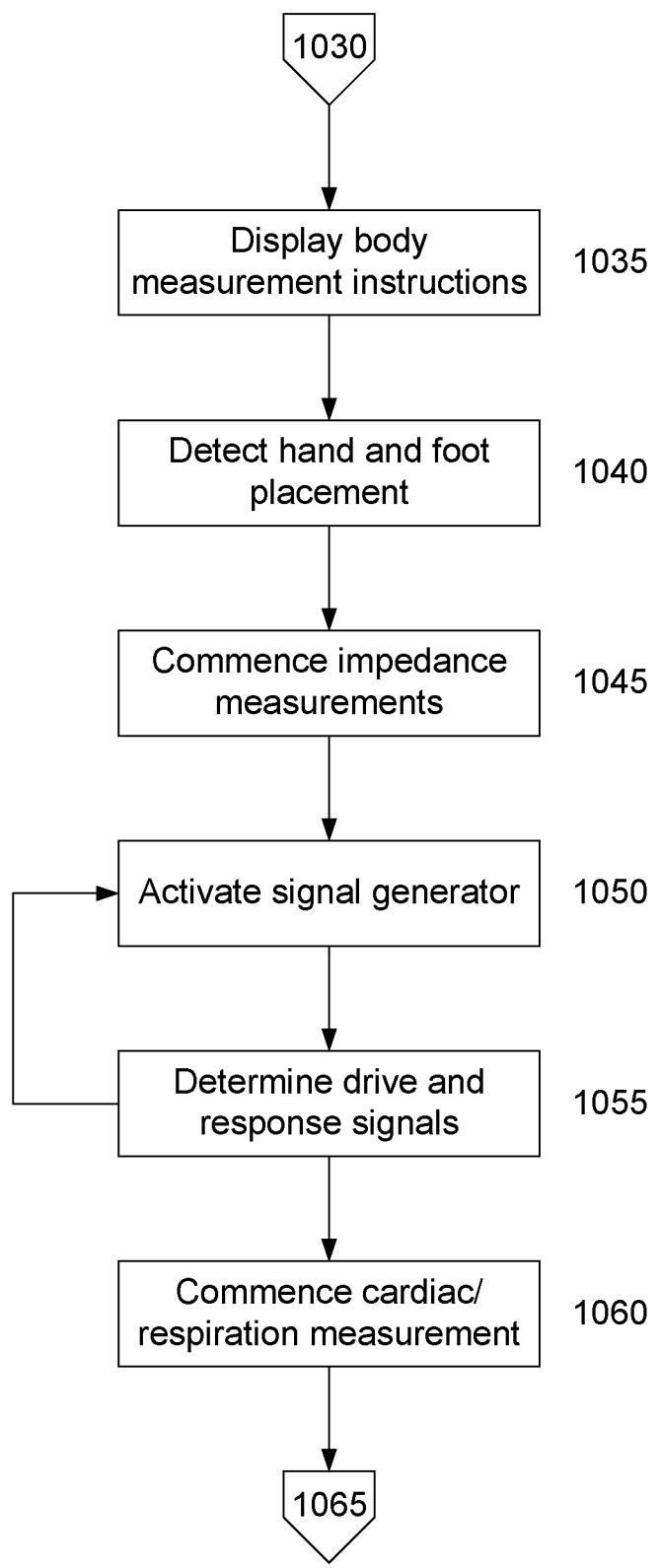
Figure 10C:
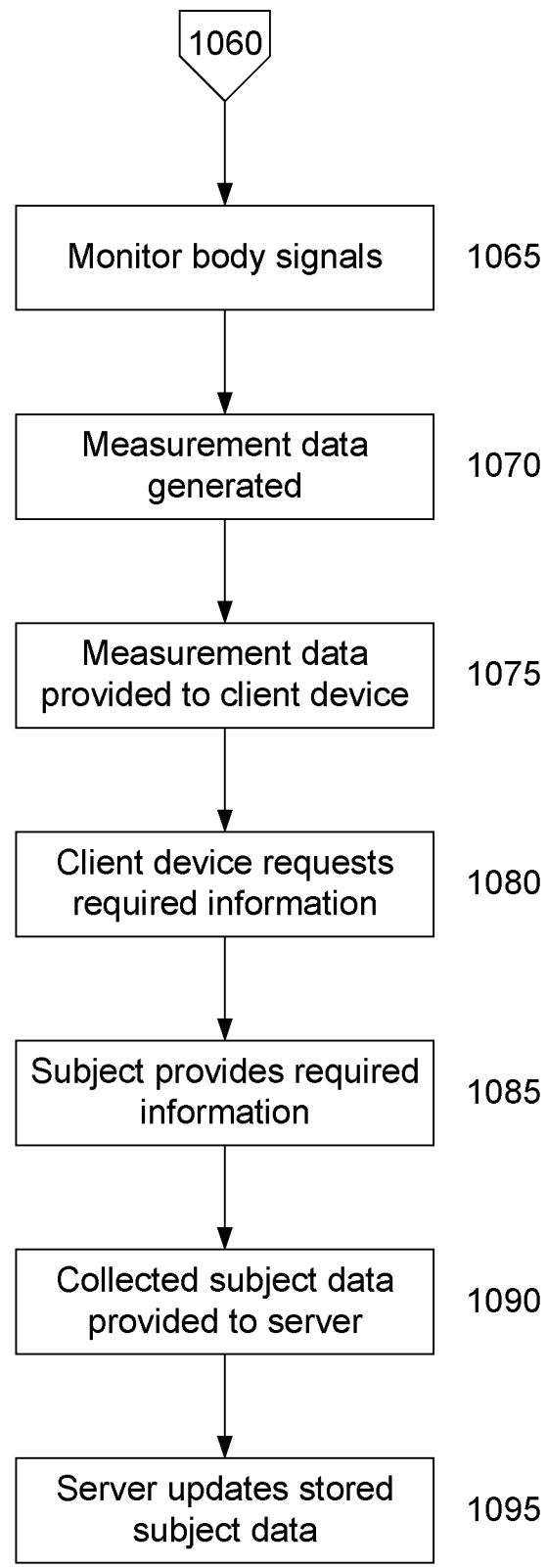

Operation of the system will now be described in further detail with reference to FIGS. 10A to 10C.

For the purpose of these examples it will also be assumed that subjects use the client devices 130 to interact with or control the measuring device 110, allowing impedance and/or other measurements to be performed and allowing information, such as information regarding physical characteristics, to be collected. This is typically achieved by having the subject interact with the system via a GUI (Graphical User Interface), or the like presented on the client device 130, which may be generated by a local application, or hosted by the server 750, which is typically part of a cloud based environment, and displayed via a suitable application, such as a browser or the like, executed by the client device 130. Actions performed by the client device 130 are typically performed by the processor 800 in accordance with instructions stored as applications software in the memory 801 and/or input commands received from a user via the I/O device 802. Similarly, actions performed by the server 750 are performed by the processor 900 in accordance with instructions stored as applications software in the memory 901 and/or input commands received from a user via the I/O device 902, or commands received from the client device.

The system utilises multiple measuring and client devices 110, 130, which interact with one or more central servers 750, typically forming part of a cloud based environment. This allows subject data to be collected from a number of different sources, and then aggregated and stored centrally, in turn allowing the system to function as an electronic medical record system.

Whilst the following example focuses on the analysis of impedance indicators only, it will be appreciated that the techniques could be extended to include other parameter values, such as other vital signs or the like, and reference to impedance indicators only is not intended to be limiting.

However, it will be appreciated that the above described configuration assumed for the purpose of the following examples is not essential, and numerous other configurations may be used. It will also be appreciated that the partitioning of functionality between the measuring device 110, client devices 130, and servers 750 may vary, depending on the particular implementation.

In this example, at step 1000 the subject optionally activates the client device 130, which would typically involve opening an application installed on the client device in order to allow the measurement process to commence.

At this time, the subject may optionally be prompted to provide authentication information, which may involve supplying biometric information, for example by performing an iris scan, fingerprint scan, or the like, or alternatively entering information such as a password, PIN or similar. As a further alternative, authentication information can be derived from the results of measurements performed below, for example by basing authentication information on a combination of measured parameters, such as a height, weight, and impedance values. Provided authentication information can then be used to authenticate and identify the subject, with this being performed locally by the client device 130, or remotely by the server 750 depending on the preferred implementation.

A measurement procedure may also be selected. In this regard a number of different measurement procedures may be implemented depending on a range of factors, such as the software modules loaded onto the client device 130, conditions suffered by the subject, body status indicators to be displayed, or the like. The process of selecting a measurement procedure can involve displaying information regarding available measurement procedures allowing a user to select one of these. Alternatively, this may be performed automatically, for example by selecting a measurement procedure based on the software installed on the device. As a further alternative this may not be required if identical measurement processes are used irrespective of the information presented to the subject.

At step 1005 the subject stands on the foot unit comprising the first housing 210, with the measuring device processor 512 detecting this based on signals from the load cells at step 1010. At step 1015, the measuring device processor 512 generates a weight measurement indication, which is provided to the client device 130 at step 1020, causing the client device to notify the subject that the weight measurement is to commence, optionally providing instructions, such as instructing the subject to stands still with their hands by their sides, to prevent the subject inadvertently resting their hands on the hand unit, thereby compromising the weight measurement. Once signals from the weight sensors have reached equilibrium, a weight measurement is performed and weight data generated.

At step 1030, the measuring device processor 512 provides the client device 130 with a body measurement indication, causing the client device to notify the subject to place their hands on the hand unit comprising the second housing 220, with their hands and in contact with the respective hand drive and sense electrodes at step 1040. Contact with the electrodes is detected by applying a drive signal to the drive electrodes and measuring the response signal to ensure successful contact has been achieved at step 1045. It will be appreciated that if this has not occurred additional instruction can be provided to the subject in a manner similar to that outlined above.

At step 1050, impedance measurements are commenced, with a sequence of drive signals being applied to respective ones of the drive electrodes, and measurements being performed via respective sense electrodes. In general, two signal generators are activated at step 1050, so that drive signals are applied via two of the drive electrodes, with response signals being detected via two of the sense electrodes at step 1055. This is repeated for different combinations of electrodes until desired measurements have been performed. In one preferred example, this process is performed to collect impedance measurements at multiple frequencies, and typically 256 or more frequencies, with this being performed to measure segmental impedance values for each limb, and the torso, as well as whole of body impedance measurements.

At step 1060, a cardiac/respiration measurement is performed, with the sensors 514 being activated to measure body signals at step 1065.

At step 1070 the measured signals are used by the measurement device processor 512 to generate measurement data. The measurement data can include raw data or may include partially or fully processed data. For example, minimal processing such as filtering of signals is typically performed by the measuring device. Additionally, voltage and current signals may be processed in order to determine impedance values such as resistance, reactance and phase angle values. For example, in the case of BIS, impedance or admittance measurements are determined from the signals at each frequency by comparing the recorded voltage and the current through the subject. The demodulation algorithm can then produce amplitude and phase signals at each frequency, allowing an impedance value at each frequency to be determined. The measurement data can include processed signals as well as raw data depending on the preferred implementation. In general inclusion of the raw data is preferred as this can allow data to be reprocessed at a later date, for example allowing this to be analysed using improved algorithms.

At step 1075 the measurement data is provided to the client device 130, typically using a short range wireless communication protocol such as Bluetooth, NFC or the like. The use of a short range protocol reduces the likelihood of the measurement data being intercepted by third parties. Irrespective of this however the measurement data can be encrypted utilising a public key of the client device. With the data also further being optionally signed by a private key of the measuring device to thereby verify the source of the measurement data and hence help ensure measurement data integrity.

At step 1080 the client device 130 may optionally request additional information, with this being provided by the subject at step 1085. This could include requesting authentication information, if this has not previously been provided. Alternatively, this could include displaying a question to the subject. The question may relate to symptoms or other information required by the system, such as information regarding physical characteristics, exercise, diet or the like, allowing additional information regarding the subject to be collected. By doing this each time a measurement is performed allows a wide range of data regarding the subject to be collected, without placing an undue burden on the subject.

It will also be appreciated that other measurements could also be performed in addition to those outlined above, for example using other suitable sensing mechanisms. For example, the client device 130 may be equipped with sensors allowing additional information, such as a subject temperature to be measured.

The measurement data is collated with any other relevant information, with collected subject data being provided to the server 750 at step 1090. The collected subject data typically includes the measurement data and any additional data, such as responses to questions, data collected from additional sensors, such as physical characteristic data, but may also include other data such as environmental data, including but not limited to location data, temperature data, of the like. The collected subject data may be encrypted using a suitable encryption mechanism, such as encrypting the collected subject data using a public key of the server 750, and optionally signing the collected subject data using a private key of the client device 130, thereby ensuring privacy of the collected subject data is maintained.

At step 1095, the server 250 updates subject data stored in the subject database 751, by adding the collected subject data. It will be appreciated that this allows subject data relating to the individual to be collected over time, which in turn enables a comprehensive health record to be established directly from measurement data recorded from a measuring device. Once subject data has been recorded, this can be used to generate a body status indicator which is displayed to the subject. The body status indicator can be displayed at any time during the process and this does not need to wait until collected subject data has been uploaded to the server. Indeed, this can be performed concurrently with the data collection process.

The nature of the body status indicator will vary depending on the preferred implementation and the nature of the measurement data. The body status indication could include a simple recorded value but more typically examined changes in parameter values such as changes in fluid levels or the like. The nature of the body status indicator is not important for the purposes of the current example and numerous body status indicators will be known to those in the art, for example as listed above.

Figure 11A:
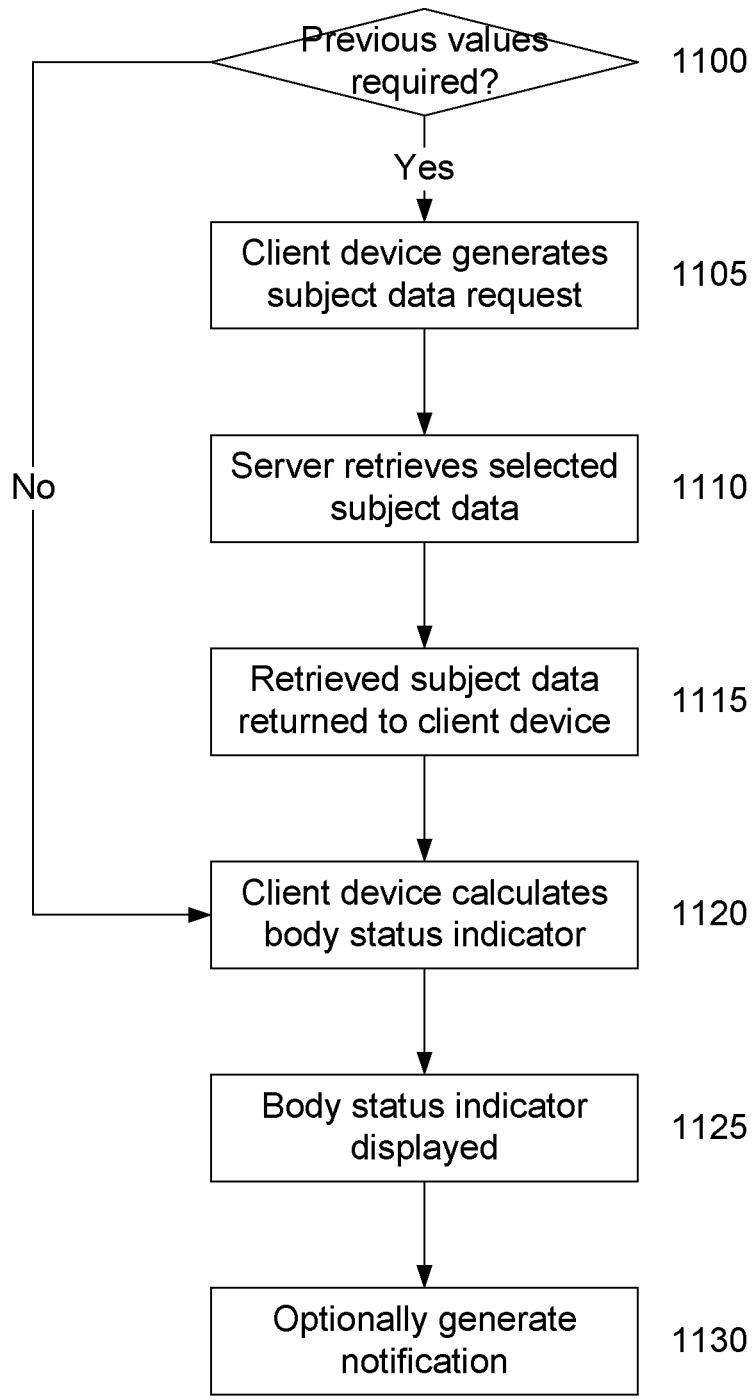
FIG. 11A is a flow chart of a first example of a process for displaying a body status indicator.

In one example the body status indicator is generated locally using the client device 130, as shown in FIG. 11A.

In this example step 1100 the client device 130 determines if previously measured body parameter values are required. It will be appreciated that these may not be required, for example if they are already stored locally on the client device 130, or if they are not needed to generate the body status indicator. Assuming previous body parameter values are required, at step 1105 the client device 130 generates a subject data request which is transferred to the server 250. At step 1110 the server 250 retrieves relevant subject data, returning this retrieved subject data to the client device 130 at step 1115. At step 1120, the client device 130 calculates the body status indicator, for example by determining a change in the body parameter value, causing this to be displayed to the subject at step 1125.

At this stage, the client device 130 may also optionally generate a notification, for example based on comparison of the body parameter value and/or body status indicator to a reference range or other notification criteria. The notification can be displayed on the client device 130, and may include a motivational message, alert, warning, or the like. For example, if the user has an unexpectedly high heart rate, or if fluid levels have changed dramatically in a short period of time, a warning may be displayed to the subject directing them to seek medical attention.

Additionally, and/or alternatively notifications can be provided to other authorised users. For example, subjects can grant specific users, such as medical practitioners, authorization to access their subject data. In this instance the client device 130 can generate a notification and transfer this to an authorised user, such as the subject's doctor, alerting them to a particular event. This can be used to allow the medical practitioner to contact the subject directing them to seek medical attention.

Figure 11B:
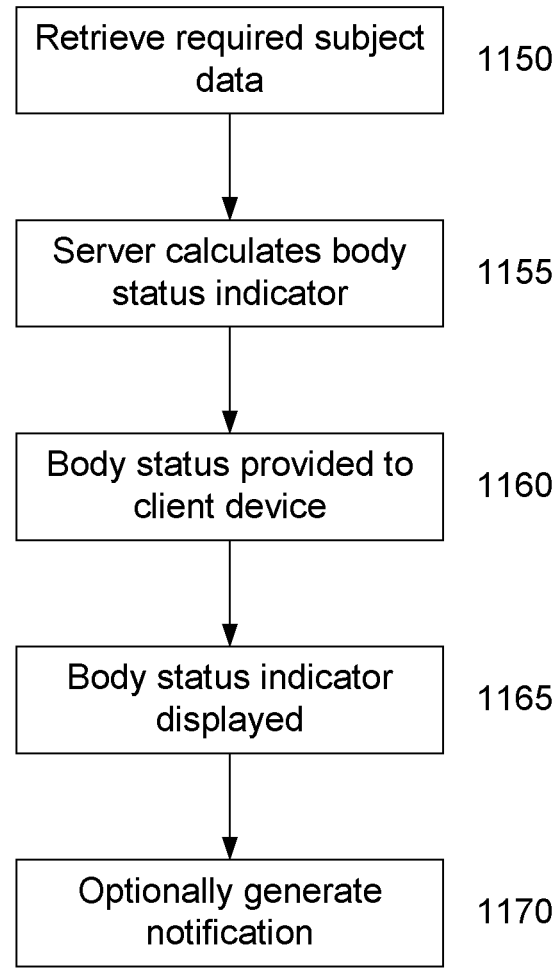
FIG. 11B is a flow chart of a second example of a process for displaying a body status indicator.

It will be appreciated that the above-described process may require that subject data is retrieved and provided to the client device 130. As an alternative to this however the body status indicator could be generated by the server 250 and transferred to the client device, and an example of this will now be described with reference to FIG. 11B.

In this example, the server 250 retrieves required subject data at step 1150 and then calculates the body status indicator at step 1155. The body status indicator is then transferred to the client device 130 at step 1160, allowing this to be displayed to the subject at step 1165. The server 250 may then optionally generate a notification at step 1170 allowing this to be provided to the client device 130 or a client device of an authorised user as required.

Figure 12:
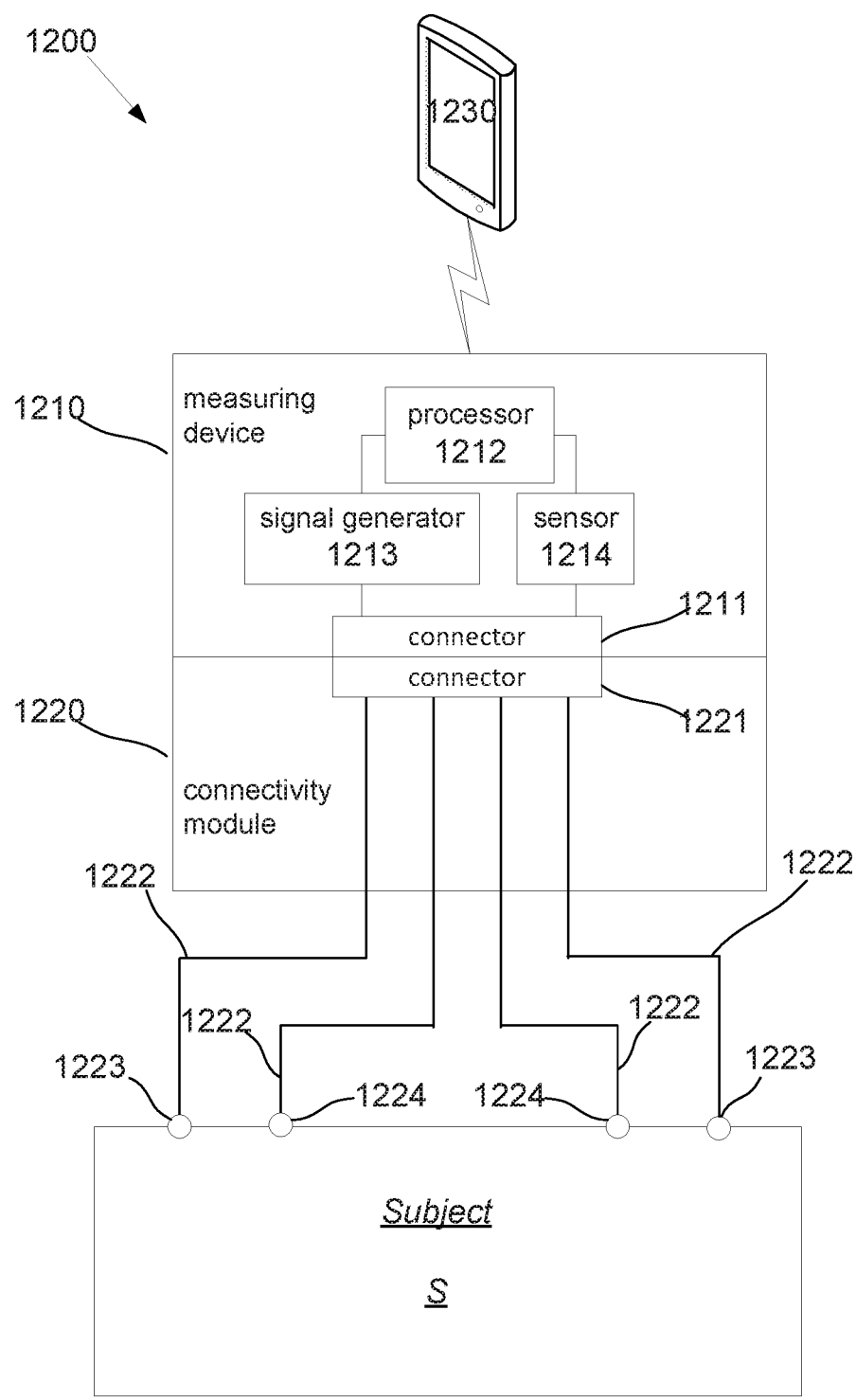
FIG. 12 is a schematic diagram of a further example of a system for performing at least one impedance measurement on a biological subject.

A further example of a measuring system will now be described with reference to FIG. 12.

In this example, the system 1200 includes a measuring device 1210 coupled to a connectivity module 1220. An optional client device, such as a computer system, smartphone, tablet or the like, can also be provided in communication with the measuring device, allowing operation of the measuring device to be at least partially controlled, although this is not essential and will depend on the preferred implementation.

The measuring device 1210 includes a measuring device housing containing at least one signal generator 1213 that generates a drive signal and at least one sensor 1214 that measures a response signal. A measuring device processor 1212 is provided that at least in part controls the signal generator 1213 and receives an indication of a measured response signal from the sensor 1214 allowing the at least one impedance measurement to be performed. The measuring device 1210 further includes a first connector 1211 electrically connected to at least the at least one sensor 1214 and the at least one signal generator 1213.

The connectivity module 1220 includes a connectivity module housing, and a number of electrodes 1223, 1224, that are provided in electrical contact with the subject S in use. The electrodes can be attached to or form part of the housing, or could be connected to the housing via respective leads 1222, and example arrangements will be described in more detail below. The connectivity module also includes a second connector 1221 electrically connected to the electrodes 1223, 1224.

In use the measuring device 1210 is connected to the connectivity module 1220 by interconnecting the first and second connectors 1211, 1221 so first electrodes 1223 are electrically connected to the at least one signal generator and second electrodes 1224 are electrically connected to the at least one sensor, thereby allowing a drive signal to be applied to the subject via the first electrodes 1223 (referred to generally as drive electrodes) and allowing the response signal to be measured via the second electrodes 1224 (referred to generally as sense electrodes) so that the at least one impedance measurement can be performed.

In the above described arrangement, a separate measuring device 1210 and connectivity module 1220 are used, allowing a single type of measuring device 1210 to be configured for use with multiple different types of connectivity module 1220. This in turn enables a range of different impedance measurements to be performed using different configurations of connectivity module. In this regard, different electrode arrangements 1223, 1224 may be required for performing different types of impedance measurement, and so the provision of a common measuring device, and different types of connectivity module allows a single measuring device to be used in a wider range of circumstances than would be possible for a single integrated device.

For example, the connectivity module 1220 could include stand-on plates and hand grip electrodes for use in measuring aspects of a subject's body composition, whilst adhesive electrodes positioned on the wrist and ankles might be preferred for oedema detection, or the like. In this instance, by allowing a common measuring device to be selectively connected to different connectivity modules, this allows the most suitable electrode configuration to be used, whilst allowing a common measuring device design to be used, which can reduce overall hardware requirements and allow for greater efficiencies in manufacture.

Furthermore, in one example, the measuring device 1210 can be adapted to sense the type of connectivity module 1220 to which it is connected, thereby at least partially controlling the impedance measurement process based on the connectivity module currently being used.

Thus, in this arrangement, a single configuration of measuring device is adapted to be used with connectivity modules that provide onward connectivity to the subject. Different types of connectivity modules can be used with the same measuring device, with the nature of the connectivity module being used to control the impedance measuring processes that can be performed. This allows a user to obtain a single measuring device and then use this with different connectivity modules, allowing different measurements to be performed. This reduces the complexity of the measuring device, and allows a single configuration of measuring device to be used in wide range of scenarios. Additionally, this allows users to only acquire connectivity modules that are relevant to measurements that are to be performed, avoiding the need to acquire unnecessary hardware. Finally, this also allows the connectivity modules to be customised for the particular measurements that are to be performed, which in turn helps ensure the electrode configuration is optimised for the particular measurements being performed.

An example of a connectivity module will now be described with reference to FIGS. 12A and 12B.

Figure 13A:
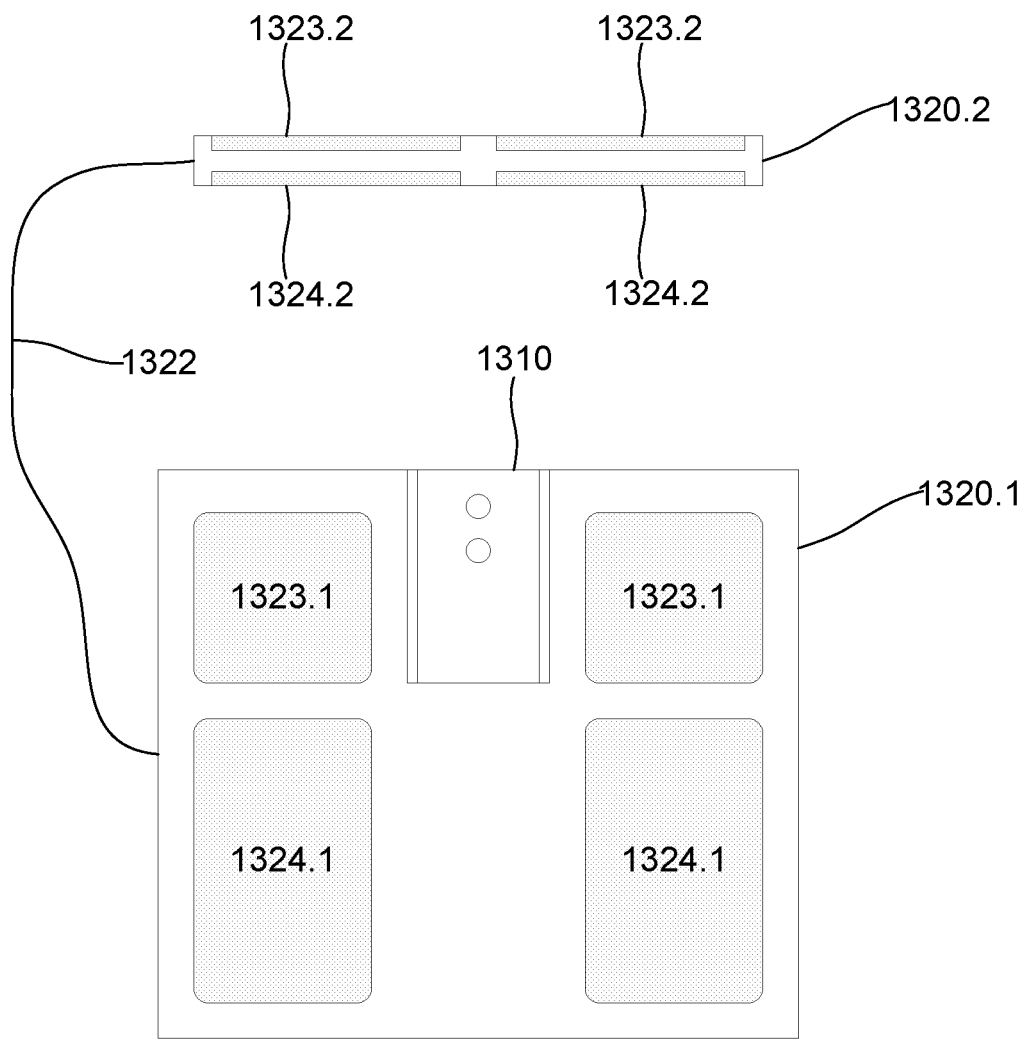
FIG. 13A is a schematic diagram of a second example of an impedance measuring system.

In the example of FIG. 13A, the connectivity module includes first and second housings 1320.1, 1320.2 which are designed for use with the feet and hands respectively. In this example, the housing 1320.1 is similar in form factor to a set of scales, and includes two spaced pairs of foot drive and sense electrodes 1323.1, 1324.1 forming footplates, on which a user can stand. Conversely, the second housing 1320.2 is in the form of a tubular body that can be grasped by a user, and which includes two spaced pairs of semi cylindrical hand drive and sense electrodes 1323.2, 1324.2 mounted on opposing sides of the body so that these contacts the subject's hands when the subject grasps the housing 1320.2. The hand drive and sense electrodes 1323.2, 1324.2 are coupled to the first housing 1320.1 and hence the connector (not shown) via one or more leads 1322. This arrangement allows the user to stand on the first housing 1320.1 and grasp the second housing 1320.2, allowing impedance measurements to be performed in a manner similar to that described above.

Figure 13B:
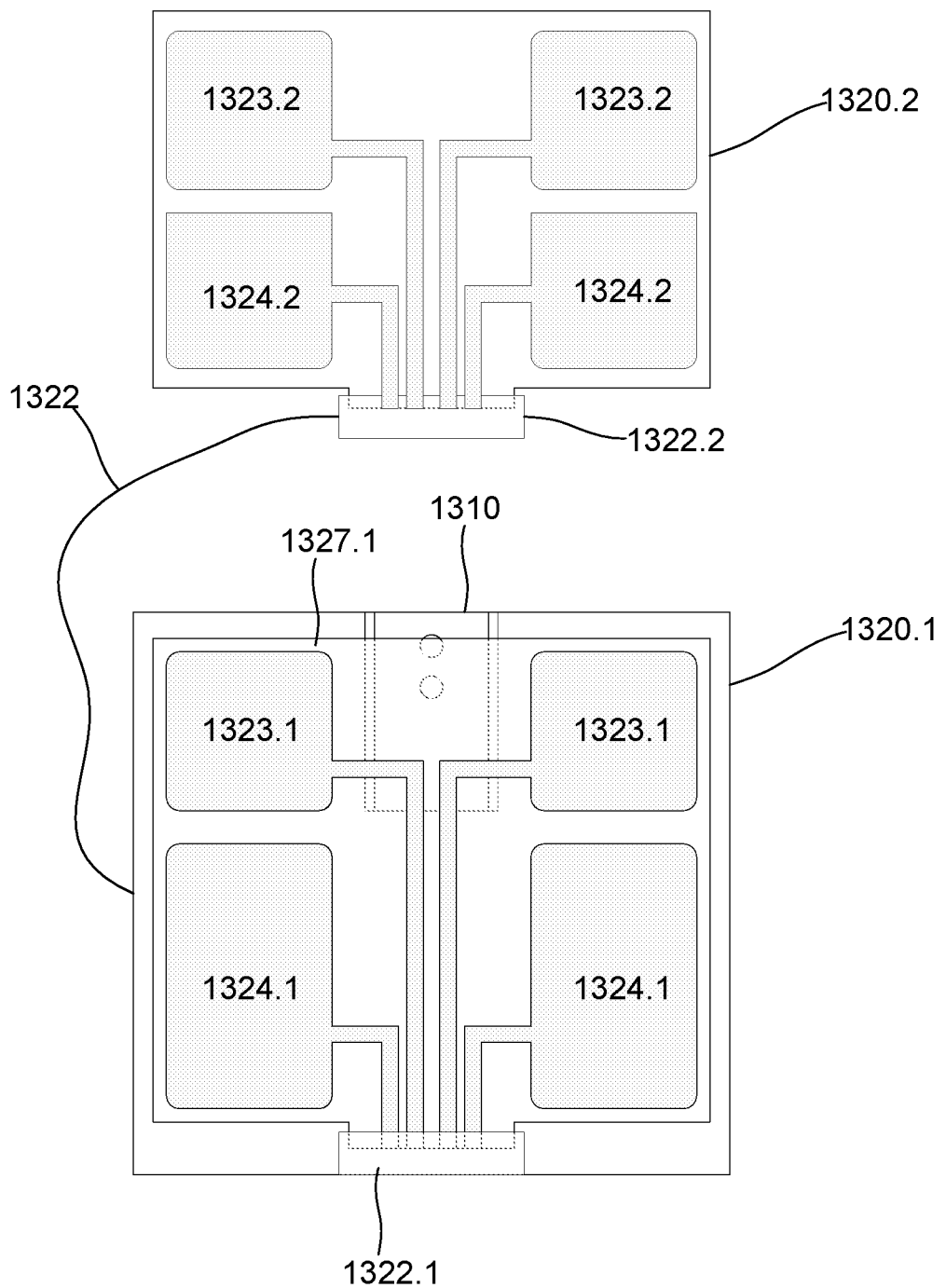
FIG. 13B is a schematic diagram of an example of an electrode sheet for the impedance measuring system of FIG. 13A.

In one example, the foot electrodes 1323.1, 1324.1 could be in the form of metal plates mounted within the first housing 1320.1. An alternative arrangement is shown in FIG. 13B. In this example, the foot electrodes 1323.1, 1324.1 could be provided on an electrode unit including a substrate 13211.1 having respective electrodes 1323.1, 1324.1 printed thereon. Tracks 13211.2 extend from the electrodes 1323.1, 1324.1 onto a tab 13211.3, which acts to provide a mounting allowing a connector 1322.1, typically mounted on the housing 1320.1, to be coupled thereto, thereby electrically connecting the electrodes 1323.1, 1324.1 to the second connector (not shown).

A similar arrangement could also be used for the hand electrodes, with a sheet having the hand electrodes 1323.2, 1324.2 printed thereon. In this instance, the hand electrode sheet could be placed on a desk or table, whilst the connectivity module housing 1320.1 is placed on the floor, allowing the impedance measurements to be performed whilst the subject is seated.

A further example is shown in FIGS. 13C and 13D.

In this example, the connectivity module 1320 again includes first and second housings 1320.1, 1320.2. The first housing 1320.1 has a form factor similar to a set of scales, and includes two spaced pairs of foot drive and sense electrodes 1323.1, 1324.1 forming footplates, on which a user can stand. The second housing 1320.2 is an elongate housing having three portions along its length, with a central rectangular portion 1302.21 positioned between two outer semicylindrical portions 1320.22. In this example, the outer semicylindrical portions 1320.22 support curved electrode plates 1323.2, 1324.2 mounted on opposing sides of the body allowing the user to place their palms and fingers on the plates 1323.2, 1324.2. In this regard, the curvature of the surface assists with comfort and ensures good physical and hence electrical contact between the user's hands and the electrodes. Meanwhile the central portion can be used to support the measuring device 1310, and also optionally a client device 1330, such as a tablet or the like, which can be used to control the measurement process as will be described in more detail below.

It will be appreciated from this that a wide variety of connectivity modules could be provided, with these being used in different circumstances to allow respective types of impedance measurement to be performed, whilst still using a common measuring device.

Thus, in the above described arrangements, the measuring device is provided in a measuring device housing that is separate to the connectivity module housing. This is beneficial in terms of facilitating use of a single measuring device with multiple different connectivity modules, particularly in terms of allowing for measuring device handling to be performed when attaching or detaching the measuring device and connectivity modules, without potential to damage components of the measuring device.

However, it will be appreciated that this is not essential, and alternatively, the measuring device could be provided within the connectivity module housing, and hence not require a separate measuring device housing. This allows the measuring device to be provided in the connectivity module housing in a manner substantially similar to that described above, albeit with the measuring device contained entirely within the connectivity module housing.

For example, the measuring device could include a circuit board, having the relevant components and first connector mounted thereon. This could be supported internally within the connectivity module, either through physical engagement between the first and second connectors, or through cooperation with a separate bracket or other mounting. Thus, it will be appreciated that this arrangement could be analogous to the manner in which a card, such as a graphics card or RAM is installed in a computer system housing through attachment to a motherboard, with the measuring device corresponding to the card, and the connectivity module the computer system and motherboard.

In this latter arrangement, it would be typical, although not essential, for the measuring device to be mounted in a single connectivity module, as opposed to being used interchangeably with different connectivity modules, to thereby ensure components of the measuring device are not damaged. Nevertheless, this would still allow for common measuring devices to be used with a wide range of different connectivity modules, thereby reducing manufacturing complexity and requirements, whilst still allowing a wide range of functionality to be achieved.

It will be appreciated that features from different examples above may be used interchangeably where appropriate. Furthermore, whilst the above examples have focused on a subject such as a human, it will be appreciated that the measuring device and techniques described above can be used with any animal, including but not limited to, primates, livestock, performance animals, such race horses, or the like. The above described processes can be used for diagnosing the presence, absence or degree of a range of conditions and illnesses, including, but not limited to oedema, lymphodema, body composition, or the like, and reference to specific indicators is not intended to be limiting.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

We claim:

1. A measuring system including:
   i) a first housing including spaced pairs of foot drive and sense electrodes being adapted to be placed in electrical contact with feet of the subject in use;
   ii) a second housing, the second housing being a single housing including spaced pairs of hand drive and sense electrodes and a support, wherein the hand drive and sense electrodes are in an upper surface of the second housing and adapted to be placed in electrical contact with hands of the subject in use, wherein the support supports a client device, the client device being adapted to be wirelessly connected to the measuring system, wherein the support is detachable from the second housing;
   iii) a stand including a leg that supports the first housing relative to the second housing;
   iv) at least one signal generator electrically connected to at least one of the drive electrodes to apply a drive signal to the subject;
   v) at least one sensor electrically connected to at least one of the sense electrodes to measure a response signal in the subject; and,
   vi) a measuring device processor that at least in part:
      (1) controls the at least one signal generator;
      (2) receives an indication of a measured response signal from the at least one sensor; and,
      (3) generates measurement data indicative of at least one measured impedance value.

2. The system of claim 1, wherein the drive and sense electrodes are spaced apart metal plates and at least one of:
   the foot drive and sense electrodes are spaced apart by at least one of:
      a) at least 8 cm;
      b) at least 8.2 cm;
      c) at least 8.4 cm;
      d) up to 9 cm;
      e) up to 8.8 cm;
      f) up to 8.6 cm;
      g) between 8 cm and 9 cm;
      h) between 8.2 cm and 8.8 cm;
      i) between 8.4 cm and 8.6 cm; and,
      j) approximately 8.5 cm;
   the foot drive electrode has a surface area that is at least one of:
      a) at least 110 cm$^2$;
      b) at least 115 cm$^2$;
      c) at least 120 cm$^2$;
      d) at least 122 cm$^2$;
      e) up to 140 cm$^2$;
      f) up to 135 cm$^2$;
      g) up to 130 cm$^2$;
      h) up to 218 cm$^2$;
      i) between 110 cm$^2$ and 140 cm$^2$;
      j) between 115 cm$^2$ and 135 cm$^2$;
      k) between 120 cm$^2$ and 130 cm$^2$;
      l) between 122 cm$^2$ and 128 cm;
      m) approximately 125 cm$^2$; and,
      n) approximately 124.3 cm$^2$; and,
   the foot sense electrode has a surface area that is at least one of:
      i) at least 35 cm$^2$;
      ii) at least 40 cm$^2$;
      iii) at least 45 cm$^2$;
      iv) at least 50 cm$^2$;
      v) up to 70 cm$^2$;
      vi) up to 65 cm$^2$;
      vii) up to 60 cm$^2$;
      viii) up to 55 cm$^2$;
      ix) between 35 cm$^2$ and 70 cm$^2$;
      x) between 40 cm$^2$ and 65 cm$^2$;
      xi) between 45 cm$^2$ and 60 cm$^2$;
      xii) between 50 cm$^2$ and 55 cm$^2$;
      xiii) approximately 53 cm$^2$; and,
      xiv) approximately 52.6 cm$^2$.

3. The system of claim 1, wherein the first housing includes a raised lip configured to engage at least a heel of the subject.

4. The system of claim 1, wherein the first housing includes feet that support the first housing spaced from a surface and wherein the feet engage load cells mounted within the first housing, the measuring device processor being adapted to determine a weight of a subject standing on the first housing.

5. The system of claim 4, wherein the first housing includes:
   a) a rigid internal plate; and,
   b) four foot assemblies, each foot assembly including:
      i) a load cell mounting on an underside of the plate;
      ii) a foot member; and,
      iii) a load cell coupled to the load cell mounting and the foot member so that the load cell deforms upon application of a load to the rigid plate.

6. The system of claim 1, wherein the hand drive and sense electrodes in each pair are metal plates and at least one of:
   the hand drive and sense electrodes are spaced apart by at least one of:
      a) at least 3 cm;
      b) at least 3.2 cm;
      c) at least 3.4 cm;
      d) up to 4 cm;
      e) up to 3.8 cm;
      f) up to 3.6 cm;
      g) between 3 cm and 4 cm;
      h) between 3.2 cm and 3.8 cm;
      i) between 3.4 cm and 3.6 cm; and,
      j) approximately 3.5 cm;
   the hand drive electrode has a surface area that is at least one of:
      a) at least 35 cm$^2$;
      b) at least 38 cm$^2$;
      c) at least 40 cm$^2$;
      d) at least 41 cm$^2$;
      e) up to 50 cm$^2$;
      f) up to 45 cm$^2$;
      g) up to 43 cm$^2$;
      h) up to 42 cm$^2$;
      i) between 35 cm$^2$ and 50 cm$^2$;
      j) between 38 cm$^2$ and 45 cm$^2$;
      k) between 40 cm$^2$ and 43 cm$^2$;
      l) between 41 cm$^2$ and 42 cm;

m) approximately 41 cm²; and,
n) approximately 41.4 cm²; and,
the hand sense electrode has a surface area that is at least one of:
a) at least 35 cm²;
b) at least 40 cm²;
c) at least 45 cm²;
d) at least 46 cm²;
e) up to 55 cm²;
f) up to 50 cm²;
g) up to 49 cm²;
h) up to 48 cm²;
i) between 35 cm² and 55 cm²;
j) between 40 cm² and 50 cm²;
k) between 45 cm² and 49 cm²;
l) between 46 cm² and 48 cm²;
m) approximately 47 cm²; and,
n) approximately 46.8 cm².

7. The system of claim 1, wherein the second housing includes a raised portion between each pair of hand drive and sense electrodes, and wherein the raised portion defining thumb recesses to thereby guide positioning of a subject's hands relative to each pair of hand drive and sense electrodes in use.

8. The system of claim 1, wherein the client device is at least one of a tablet and a smartphone.

9. The system of claim 1, wherein at least one of:
a) the leg is curved so that a centre of the platform is offset from a centre of the base;
b) the leg includes a cavity that receives a lead extending between the first and second housings;
c) the first housing is spaced from the second housing by a vertical distance of at least one of:
i) at least 100 cm;
ii) at least 103 cm;
iii) at least 104 cm;
iv) at least 105 cm;
v) up to 110 cm;
vi) up to 108 cm;
vii) up to 107 cm;
viii) up to 106 cm;
ix) between 100 cm and 110 cm;
x) between 103 cm and 108 cm;
xi) between 104 cm and 107 cm;
xii) between 105 cm and 106 cm;
xiii) approximately 105.5 cm; and,
xiv) 105.4 cm.

10. The system of claim 2, wherein the measuring system includes:
a) four signal generators, each signal generator being electrically connected to a respective drive electrode; and,
b) four sensors, each sensor being electrically connected to at least one of the sense electrodes to measure a response signal in the subject and wherein the measuring device processor selectively controls the four signal generators and four sensors to perform a sequence of impedance measurements, the impedance measurements including at least one of:
i) segmental impedance measurements; and,
ii) whole of body impedance measurements.

11. The system of claim 1, wherein the first housing and the second housing are removably mounted to the stand.

12. The system of claim 8, wherein the client device is a smartphone.

13. The system of claim 8, wherein the client device is a tablet.

14. The system of claim 9, wherein the leg is curved so that a centre of the platform is offset from a centre of the base.

15. The system of claim 9, wherein the leg includes a cavity that receives a lead extending between the first and second housings.

16. The system of claim 9, wherein the first housing is spaced from the second housing by a vertical distance of between 100 cm and 110 cm.

17. The system of claim 10, wherein the impedance measurements include segmental impedance measurements.

18. The system of claim 10, wherein the impedance measurements include whole of body impedance measurements.

* * * * *